United States Patent
Tsai

(10) Patent No.: US 11,371,037 B1
(45) Date of Patent: Jun. 28, 2022

(54) ZINC-CHARGED PANCREATIC ENZYMES FOR TREATMENT OF CANCER AND INFLAMMATION

(71) Applicant: America Great Health, a California Corporation, Alhambra, CA (US)

(72) Inventor: David Men Hwei Tsai, Alhambra, CA (US)

(73) Assignee: America Great Health, Alhambra, CA (US)

( * ) Notice: Subject to any disclaimer, the term of this patent is extended or adjusted under 35 U.S.C. 154(b) by 0 days.

(21) Appl. No.: 17/374,357

(22) Filed: Jul. 13, 2021

(51) Int. Cl.
    *C12N 9/94*     (2006.01)
    *A61P 35/00*     (2006.01)
    *A61K 38/00*     (2006.01)

(52) U.S. Cl.
    CPC ................ *C12N 9/94* (2013.01); *A61P 35/00* (2018.01); *A61K 38/00* (2013.01)

(58) Field of Classification Search
    CPC ............................ C12N 9/6427; C12N 9/2414
    See application file for complete search history.

(56) References Cited

PUBLICATIONS

Agarwal et al. 1987; Metal binding characteristics of human salivary and porcine pancreatic amylase. J. Bio. Chem. 262(6): 2568-2575.*

Vallee et al. 1959; Metal contentof alpha-amylases of various origins. J. Biol. Chem. 234(11): 2901-2905.*

Maares M, Haase H, A Guide to Human Zinc Absorption: General Overview and Recent Advances of In Vitro Intestinal Models, Nutrients, 2020;12(3):762. Published Mar. 13, 2020. doi:10.3390/nu12030762.

Petukh, M. et al., Predicting Nonspecific Ion Binding Using DelPhi, Biophysical Journal, Jun. 2012, vol. 102, 2885-2893, Published 2012 by Biophysical Society, doi: 10.1016/j.bpj.2012.05.013.

\* cited by examiner

*Primary Examiner* — Karen Cochrane Carlson
(74) *Attorney, Agent, or Firm* — Trojan Law Offices

(57) ABSTRACT

This invention is directed to pancreatic enzymes that have been charged with zinc ions, or zinc-charged pancreatic enzymes. Charging the pancreatic enzymes with zinc ions activate the pancreatic enzyme's anticancer and anti-inflammation properties and make the enzymes capable of being administered orally. It is observed that the zinc-charged pancreatic enzymes are able to induce apoptosis in various cancer cells without affecting the normal cells. The zinc-charged pancreatic enzymes have also been observed inducing apoptosis in trophoblasts and reducing inflammation in general. This invention is further directed to a method of preparing zinc-charged pancreatic enzymes. This invention is further directed to a method of treating cancer and inflammation using the zinc-charged pancreatic enzymes.

20 Claims, 18 Drawing Sheets

ZINC-CHARGED PANCREATIC ENZYMES FOR TREATMENT OF CANCER AND INFLAMMATION

FIELD OF THE INVENTION

The present invention relates generally to zinc-charged pancreatic enzymes that induce apoptosis in various cancer cells and trophoblasts, thereby treating cancer and inflammation.

BACKGROUND OF THE INVENTION

Since the early 20$^{th}$ century, it has been theorized that pancreatic enzymes may be effective in treating cancer. Scottish scientist John Beard in the early 20$^{th}$ century observed that the trophoblast of the placenta shares similarity to cancer cells in that both cell types are highly invasive and poorly differentiated. He also observed that the fetus started secreting pancreatic enzymes in approximately the second month of fetal development, a coincidence with the termination of placenta continual invasiveness into the mother's uterus. Since a fetus does not need digestive enzymes as a fetus receives all the nutrients directly from the mother, this coincidence suggested that pancreatic enzymes must play a role in controlling trophoblast invasion.

Trophoblasts are specialized cells that form the outer layer of a blastocyst. They are generally present four days post-fertilization in humans. These specialized cells provide nutrients to the embryo and develop into a large part of the placenta. Trophoblasts play an important role in embryo implantation and interaction with the decidualized maternal uterus. The invasion of a specific type of trophoblast into the maternal uterus is a vital stage in the establishment of pregnancy. Failure of the trophoblast to invade sufficiently is important in the development of pre-eclampsia. On the other hand, invasion of the trophoblast too deeply may cause conditions such as placenta ac, placenta increta, or placenta percreta. It was found that trophoblasts start to invade a maternal uterus in the first three weeks of gestation and stops in the second month of gestation.

Giving the similarity between trophoblast and cancer, Beard had thus postulated that pancreatic enzymes may be used to control cancer invasion and growth and may be effective in treating cancer. However, even though this theory has been around for a long time, this theory has not been met with success. This is due to studies on invitro cell cultures showing that normal pancreatic enzymes, or "uncharged" pancreatic enzymes, fail to show any effect on trophoblasts or cancer cell lines, neither on cell growth nor cell death.

The pancreas produces numerous enzymes, including but not limited to trypsin, elastase, carboxypeptidase, amylase, and chymotrypsin, as well as hormones such as insulin. Each of these enzymes have their own functions in the human body. One of these enzymes, amylase, has been found in high levels in the plasma during pregnancy. This finding indicates that pancreatic enzymes may have an effect on trophoblasts, and thus potentially cancer cells. However, prior to the concepts disclosed herein, these pancreatic enzymes had not been shown to contain any anticancer or apoptotic activity.

One of the more recent approaches to treating cancer is based on the biological phenomena called "apoptosis." Apoptosis is also called "programmed cell death" or "cell suicide". In contrast to the cell death caused by cell injury, apoptosis is an active process of gene-directed, cellular self-destruction that serves a biologically meaningful function. One example of the biologically meaningful function of apoptosis occurs during the morphogenesis of an embryo. In fact, apoptosis plays a key role in the human body from the early stages of embryonic development through to the inevitable decline associated with old age.

Treating cancer using apoptosis is an attractive cancer treatment because it essentially teaches the cancer cells to commit suicide, thereby killing the cancer cells. Nevertheless, since the objective of cancer treatment is to kill cancer cells without killing the host, the success of this treatment is still dependent on selective apoptosis in tumor cells without affecting normal cells.

Even with the theory regarding pancreatic enzymes having anticancer properties, after over one hundred years of research, these pancreatic enzymes had not yet been shown to have any anticancer or apoptotic activity.

Additionally, these pancreatic enzymes, as with other proteins and macromolecules, are not capable of being administered orally. This is due to these proteins and other macromolecules being unable to survive the acidic conditions of the stomach, such that they are not able to be absorbed by the gastrointestinal tract and delivered throughout the body. Thus, it is current practice to not orally administer these pancreatic enzymes, as with other proteins and macromolecules.

Surprisingly, it was found that when these pancreatic enzymes were charged with zinc ions, the enzymes became apoptotic on trophoblasts and cancer cells without effecting the normal cell lines. In other word, these pancreatic enzymes needed zinc to work as a co-factor to be able to induce apoptosis on trophoblast for the termination of the further invasion of the trophoblast. This logic makes physiological sense given the fact that zinc is an essential nutrient regulating embryonic development. More importantly, given the similarity between trophoblast and cancer cells, these pancreatic enzymes may be used as an anticancer agent when it is charged with zinc.

SUMMARY OF THE INVENTION

The present invention is generally directed to pancreatic enzymes that have been charged with zinc ions ("zinc-charged pancreatic enzymes") to activate the pancreatic enzyme's anticancer and anti-inflammation properties. The present invention is further directed to a method of preparing zinc-charged pancreatic enzymes.

It is an object of this invention to provide pancreatic enzymes that have been charged with zinc, such that the zinc-charged pancreatic enzymes provide anticancer activity, for example, by inducing apoptosis in cancer cells. It is a further object of this invention to provide pancreatic enzymes that have been charged with zinc, such that the zinc-charged pancreatic enzymes provide anti-inflammatory activity. It is a further object of this invention to provide pancreatic enzymes that have been charged with zinc, such that the pancreatic enzymes may be administered orally. It is a further object of this invention to provide a method for preparing zinc-charged pancreatic enzymes such that the pancreatic enzymes' anticancer and anti-inflammation properties are activated.

Additionally, as the zinc-charged pancreatic enzymes have been shown to induce apoptosis in trophoblasts and cancer cells without affecting the normal cells, it is another object of this invention to provide a method of treating cancer and inflammation using the zinc-charged pancreatic enzymes.

BRIEF DESCRIPTION OF THE DRAWINGS

These and other features and advantages of the present invention will become appreciated, as the same becomes better understood with reference to the specification, claims and drawings herein:

DETAILED DESCRIPTION OF THE INVENTION

Figure 1A:
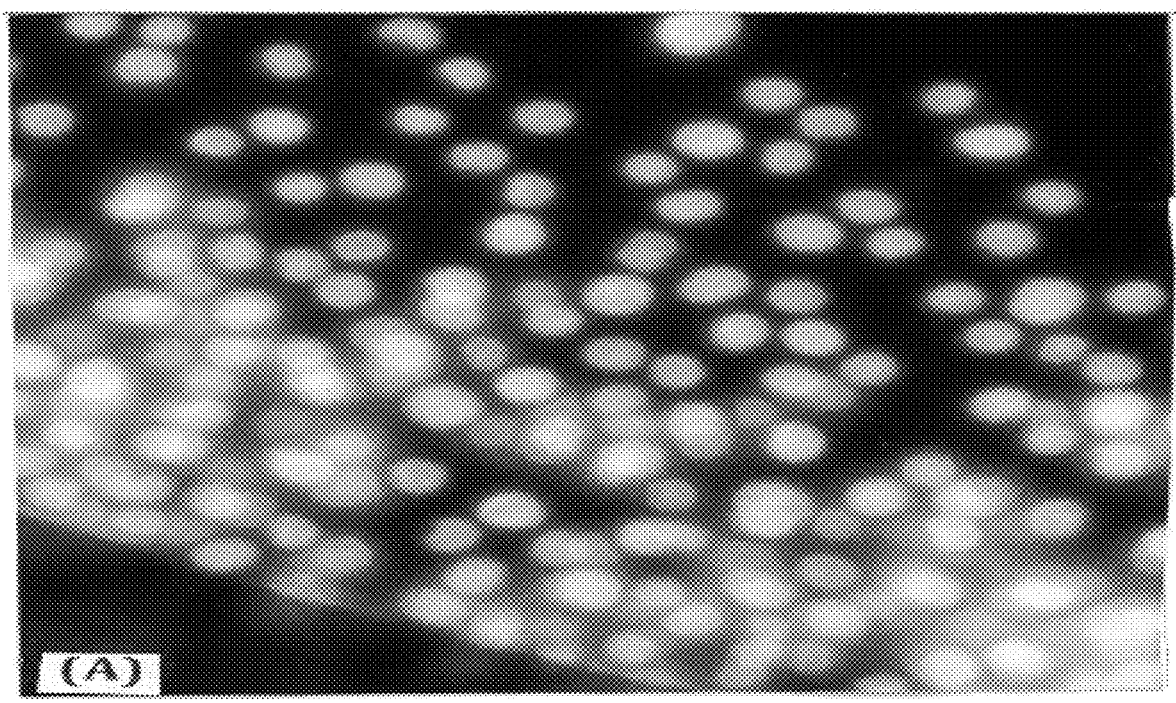
FIG. 1A is a slide of an HTR-8 trophoblast cell line incubated with a zinc-buffer solution, stained with Hoechst dye, and examined under fluorescence.

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

It will be understood that when an element is referred to as being "on" another element, it can be directly on the other element or intervening elements may be present there between. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section.

As used herein, the singular forms "a," "an," and "the," are intended to include the plural forms as well, unless the context clearly indicates otherwise. It will be further understood that the terms "comprises" and/or "comprising," "includes" and/or "including," and "have" and/or "having,"

when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom," and "upper" or "top," and "inner" or "outer," may be used herein to describe one element's relationship to another elements as illustrated in the Figures. It will be understood that relative terms are intended to encompass different orientations of the device in addition to the orientation depicted in the Figures.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing.

This patent application generally describes pancreatic enzymes that have been charged with zinc ions to activate the pancreatic enzyme's anticancer and anti-inflammation properties. In particular, this application discloses zinc-charged pancreatic enzymes, which are pancreatic enzymes that have been charged with zinc ions. Further, this application discloses a method of preparing zinc-charged pancreatic enzymes. The zinc-charged pancreatic enzymes have been shown to induce apoptosis in trophoblasts and cancer cells without affecting the normal cells. Thus, a method of treating cancer and inflammation using the zinc-charged pancreatic enzymes is also disclosed.

1. Zinc-Charged Pancreatic Enzymes

Generally, uncharged pancreatic enzymes do not exhibit any anticancer or anti-inflammatory responses. However, once the pancreatic enzymes were charged with zinc ions, the pancreatic enzymes began exhibiting anticancer and anti-inflammation behavior. The zinc-charged pancreatic enzymes exhibited anticancer properties by inducing apoptosis in various cancers and trophoblasts without affecting normal cell lines.

The first pancreatic enzyme that was explored was amylase, as amylase is found in high levels in the plasma during pregnancy. It was determined that when amylase was charged with zinc ions, the zinc-charged amylase induced apoptosis in cancer cells and trophoblasts, thereby exhibiting anticancer properties.

Once it was established that zinc-charged amylase exhibits anticancer properties, other pancreatic enzymes were also charged with zinc to determine if the other pancreatic enzymes also exhibited the anticancer behavior when zinc-charged. It was determined that the other pancreatic enzymes, including but not limited to trypsin, elastase, carboxypeptidase, chymotrypsin, and pancreatin (a mixture of various pancreatic enzymes), each induced apoptosis in cancer cells upon zinc-charging. This result suggests that the induction of apoptosis in cancer cells by zinc-charged pancreatic enzymes is a ubiquitous phenomenon. These pancreatic enzymes needed to be zinc-charged in order to activate their anticancer properties.

Additionally, it was determined that these zinc-charged pancreatic enzymes exhibited anti-inflammatory properties as well. The zinc-charged pancreatic enzymes exhibited anti-inflammatory properties by reducing the secretion of Tumor Necrosis Factor a (TNF-a), Interleukin 8 (IL-8), and Interleukin 6 (IL-6) in response to the injection of lipopolysaccharide (LPS) in mice. The reduction of these inflammatory immune molecules in mice suggested that the zinc-charged pancreatic enzymes also have anti-inflammatory properties along with the anticancer properties observed.

Furthermore, the charging of these pancreatic enzymes with zinc not only activated the pancreatic enzyme's anticancer and anti-inflammatory properties, but also allowed the zinc-charged pancreatic enzymes to become available for oral administration. This is due to the pancreatic enzymes having a "zinc-ion cloud" on the surface of the pancreatic enzymes once the pancreatic enzymes are zinc-charged. The zinc-ion cloud on the surface of the zinc-charged pancreatic enzymes both protect the pancreatic enzymes from the acidic conditions of the stomach and aid in the absorption of the pancreatic enzymes by the gastrointestinal (GI) tract.

Specifically, the zinc in the zinc-ion clouds is known to degrade hydrochloric acid by the following chemical reaction: $Zn + 2HCl \rightarrow ZnCl_2 + H_2$. Further, the hydrochloric acid and acidic conditions of the stomach are required for the peptic enzymes in the stomach to digest proteins. Thus, the zinc ions neutralizing the hydrochloric acid in the stomach prevent both the hydrochloric acid and the peptic enzymes from dissolving and digesting the pancreatic enzymes. Therefore, the zinc-charged pancreatic enzymes are capable of surviving the stomach due to this zinc-ion cloud.

Once the zinc-charged pancreatic enzymes pass through the stomach and enter the GI tract, the presence of the zinc-ion cloud further aids in the absorption of the pancreatic enzymes into the blood stream. The potential reason behind the zinc-ion cloud aiding in the absorption of the pancreatic enzymes by the intestine is that zinc is absorbed in the intestine through a "Zinc Transporter," which is a group of zinc-binding proteins in the intestine villi. The zinc-ion cloud of the zinc-charged pancreatic enzymes may interact with these Zinc Transporters, thereby transporting the zinc-charged pancreatic enzymes from the intestine villi to the blood stream. Thus, these Zinc Transporters may help the zinc-charged pancreatic enzymes be absorbed by the intestine, thereby allowing a significant amount of the pancreatic enzymes to be absorbed by the blood stream.

Thus, zinc-charged pancreatic enzymes are orally available and display anticancer and anti-inflammatory properties such that certain types of cancer may be treated using the zinc-charged pancreatic enzymes disclosed.

A. Zinc-Charged Amylase

The first pancreatic enzyme researched regarding inducing apoptosis in cancer cells and trophoblasts was amylase. Specifically, once amylase was zinc-charged using the method disclosed herein, it was determined that the zinc-charged amylase (1) induced apoptosis in various cancer cells and trophoblasts without affecting normal cell lines, (2) reduced PD-L1 expression in HT-29 cells (colon adenocarcinoma), (3) significantly reduced the secretion of TNF-a, IL-8, and IL-6 in response to the injection of LPS in mice, (4) down regulated the expression of oncogene C-Myc in HT-29 cell lines, and (5) suppressed the growth of breast cancer in an MDA-MB-23 mice model. Taking each of these determinations together suggests that zinc-charged amylase has anticancer and anti-inflammatory activity.

Figure 1B:
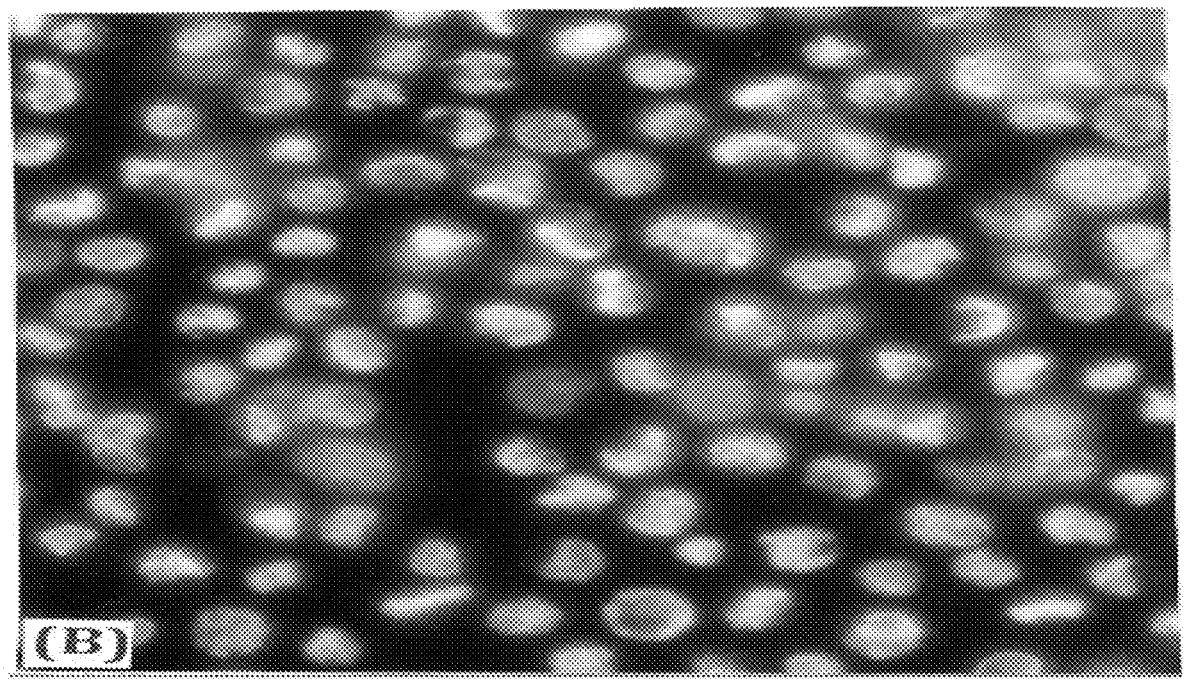
FIG. 1B is a slide of an HTR-8 trophoblast cell line incubated with a zinc-charged amylase, stained with Hoechst dye, and examined under fluorescence.
Figure 1C:
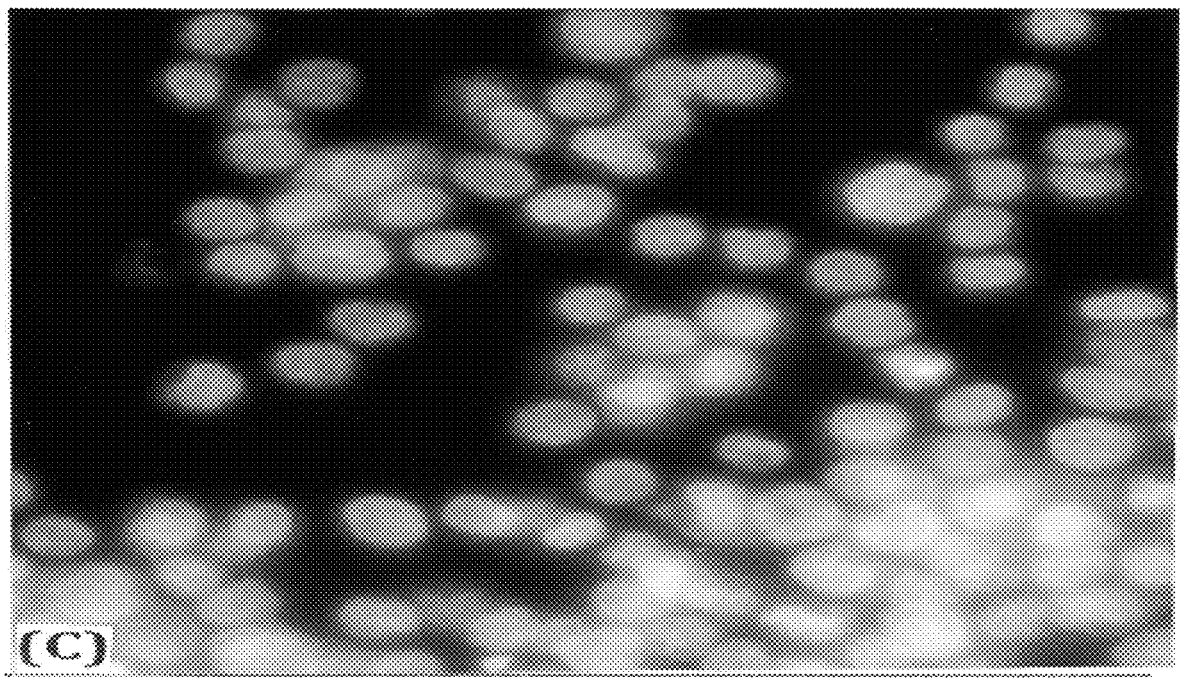
FIG. 1C is a slide of an HTR-8 trophoblast cell line incubated with an uncharged amylase, stained with Hoechst dye, and examined under fluorescence.

First, it was determined that the zinc-charged amylase induced apoptosis in cancer cells and trophoblasts without affecting normal cell lines. FIGS. 1A-1C (together FIG. 1) depict the results of Hoechst dying and observing under fluorescence a trophoblast cell line (HTR-8) treated with three separate compositions. FIG. 1A depicts HTR-8 cells that were incubated with a Tris-HCL buffer (pH 7.0) and zinc for 12 hours. FIG. 1B depicts HTR-8 cells that were incubated with 0.05 mM zinc-charged amylase for 12 hours. FIG. 1C depicts HTR-8 cells that were incubated with 0.05 mM uncharged amylase for 12 hours. Once each cell line was incubated with each respective composition for 12 hours, the cells were stained with Hoechst dye for DNA and examined under fluorescence.

As shown in FIGS. 1A & 1C, the HTR-8 cell lines that were incubated with the zinc-buffer solution (1A) and the uncharged amylase (1C) did not display any apoptotic activity or other activity. However, the HTR-8 cell lines that were incubated with the zinc-charged amylase, as shown in FIG. 1B, displayed DNA condensation, DNA breakage, and crescent-shape DNA, all of which are typical morphologies for cells undergoing apoptosis. Thus, FIG. 1 shows that normal zinc compositions, as well as uncharged amylase, do not have an apoptotic effect on trophoblasts. Yet, once the amylase was charged with zinc, the zinc-charged amylase induced apoptosis in the trophoblast cell line.

Figure 2A:
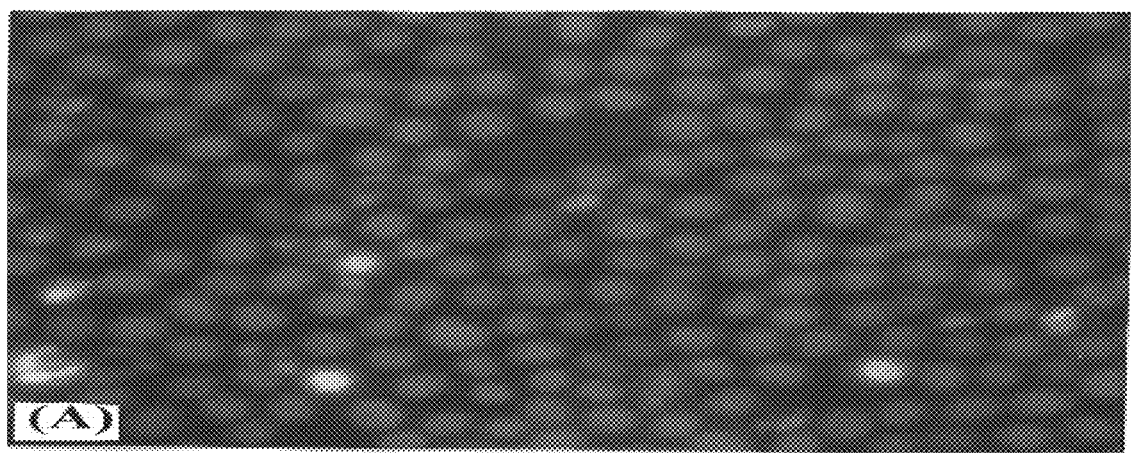
FIG. 2A is a slide of an HL-60 cancer cell line incubated with a zinc-buffer solution, stained with Hoechst dye, and examined under fluorescence.
Figure 2B:
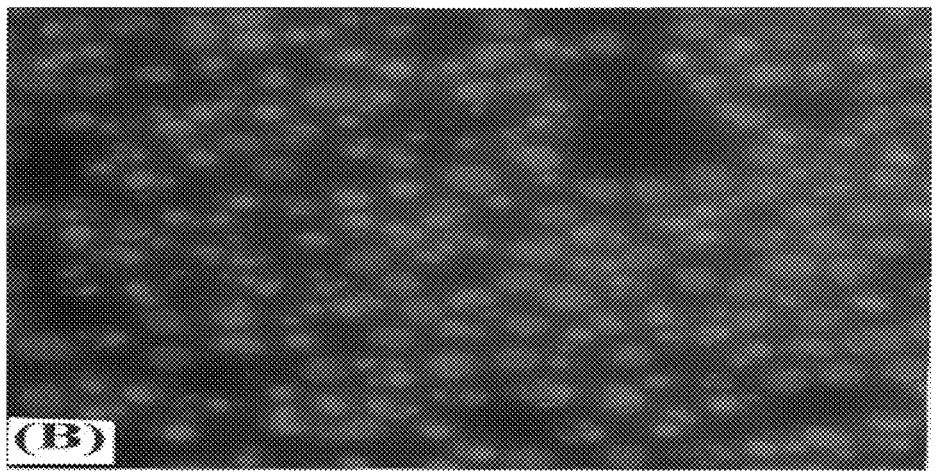
FIG. 2B is a slide of an HL-60 cancer cell line incubated with a zinc-charged amylase, stained with Hoechst dye, and examined under fluorescence.
Figure 2C:
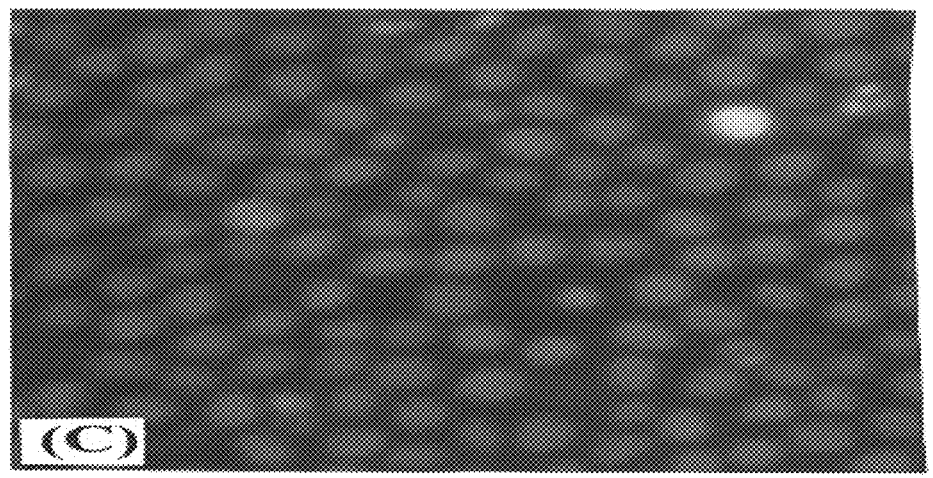
FIG. 2C is a slide of an HL-60 cancer cell line incubated with an uncharged amylase, stained with Hoechst dye, and examined under fluorescence.

FIGS. 2A-2C (together FIG. 2) depict the results of Hoechst dying and observing under fluorescence HL-60 cells (a human leukemia cell line) treated with three separate compositions. FIG. 2A depicts HL-60 cells that were incubated with a Tris-HCL buffer (pH 7.0) and zinc for 12 hours. FIG. 2B depicts HL-60 cells that were incubated with 0.05 mM zinc-charged amylase for 12 hours. FIG. 2C depicts HL-60 cells that were incubated with 0.05 mM uncharged amylase for 12 hours. Once each HL-60 cell line was incubated with each respective composition for 12 hours, the cells were stained with Hoechst dye for DNA and examined under fluorescence.

As shown in FIGS. 2A & 2C, the HL-60 cell lines that were incubated with the zinc-buffer solution (2A) and the uncharged amylase (2C) did not display any apoptotic activity or other activity. However, the HL-60 cell line that were incubated with the zinc-charged amylase, as shown in FIG. 2B, displayed DNA condensation, DNA breakage, and crescent-shape DNA, all of which are typical morphologies for cells undergoing apoptosis. Thus, FIG. 2 shows that normal zinc compositions, as well as uncharged amylase, do not have an apoptotic effect on cancer cells such as the HL-60 cell line. Yet, once the amylase was charged with zinc, the zinc-charged amylase induced apoptosis in the HL-60 cell line.

Figure 3A:
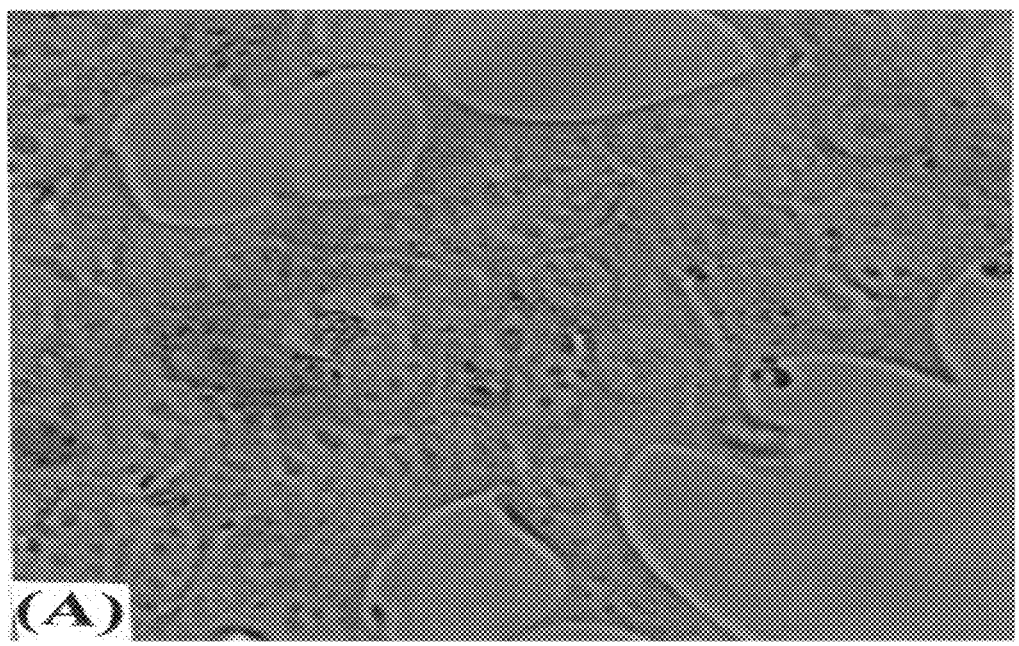
FIG. 3A is a slide of an LNCaP cancer cell line incubated with a zinc-buffer solution observed by a phase contrast microscope.
Figure 3B:
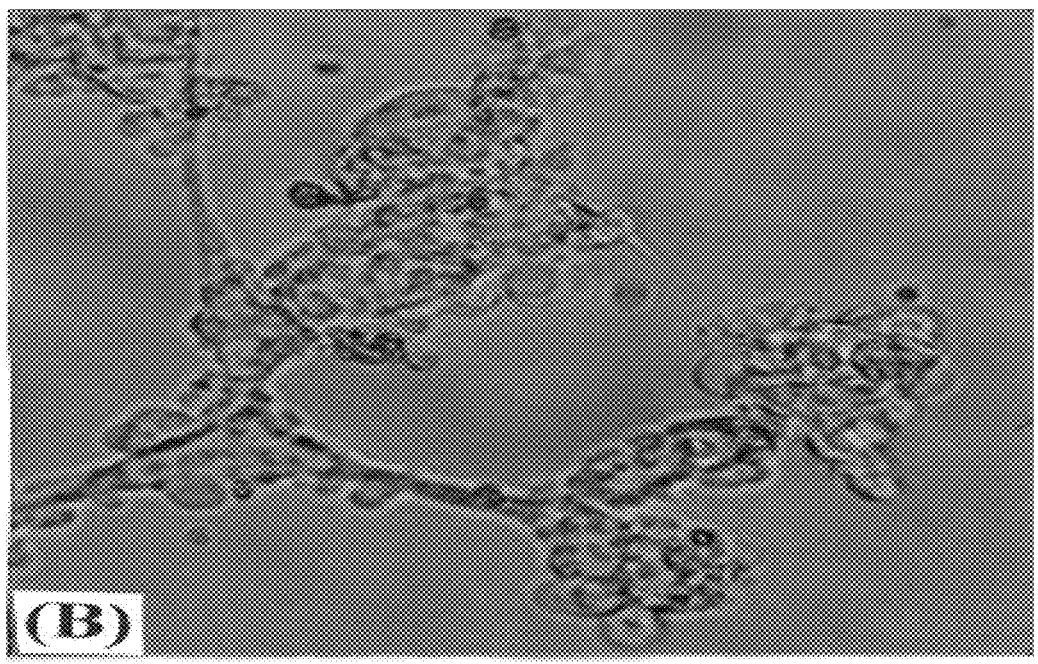
FIG. 3B is a slide of an LNCaP cancer cell line incubated with a zinc-charged amylase observed by a phase contrast microscope.
Figure 3C:
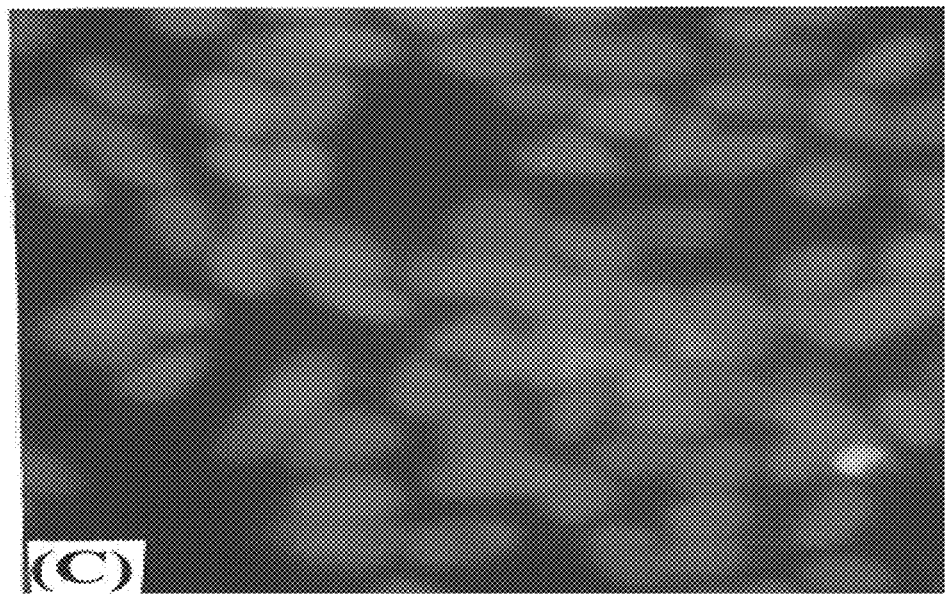
FIG. 3C is a slide of an LNCaP cancer cell line incubated with a zinc-buffer solution, stained with Hoechst dye, and examined under fluorescence.
Figure 3D:
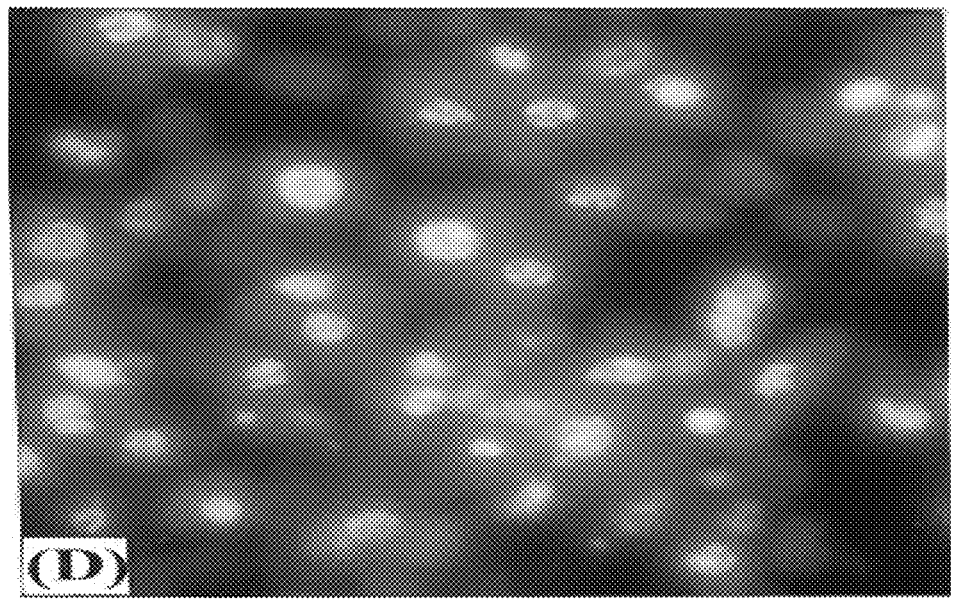
FIG. 3D is a slide of an LNCaP cancer cell line incubated with a zinc-charged amylase, stained with Hoechst dye, and examined under fluorescence.

FIGS. 3A-3D depict the apoptotic effect of the zinc-charged amylase on LNCaP cancer cells (prostate cancer). Specifically, FIGS. 3A-3B depict the LNCaP cells treated with two separate compositions observed by a phase contrast microscope. FIGS. 3C-3D depict the results of Hoechst dying and observing under fluorescence LNCaP cells treated with the same two compositions. FIGS. 3A and 3C depict LNCaP cells that were incubated with a Tris-HCL buffer (pH 7.0) and zinc for 12 hours. FIGS. 3B and 3D depicts LNCaP cells that were incubated with 0.05 mM zinc-charged amylase for 12 hours. For FIGS. 3A and 3B, once each LNCaP cell line was incubated with each respective composition for 12 hours, the cell lines were observed by a phase contrast microscope. For FIGS. 3C and 3D, once each LNCaP cell line was incubated with each respective composition for 12 hours, the cells were stained with Hoechst dye for DNA and examined under fluorescence.

As shown in FIGS. 3A & 3C, the LNCaP cell line that was incubated with the zinc-buffer solution did not display any apoptotic activity or other activity. However, the LNCaP cell line that was incubated with the zinc-charged amylase, as shown in FIGS. 3B and 3D, was found to have shrinkage and membrane blebbing, another typical morphology for cells undergoing apoptosis. Thus, FIG. 3 shows that normal zinc compositions do not have an apoptotic effect on cancer cells such as the LNCaP cell line. Yet, once the amylase was charged with zinc, the zinc-charged amylase induced apoptosis in the LNCaP cell line.

Similar results were also observed for other cancer cell lines. As discussed above, the zinc-charged amylase induced apoptosis in both the HL-60 leukemia cell line and the LNCaP prostate cancer cell line. It was similarly observed that the zinc-charged amylase also induced apoptosis in the HT-29 cell line (colon adenocarcinoma) as well as the Colo205 cell line (colon cancer). Thus, this determination suggests that zinc-charged amylase is capable of inducing apoptosis in multiple cancer cell lines, as well as trophoblasts.

Next, it was determined that the zinc-charged amylase reduced PD-L1 expression in HT-29 cancer cells. PD-L1 expressed on cancer cells functions to inactivate T-cells, which in turn prevents the T-cells from attacking the cancer cells. Thus, reducing the activity of PD-L1 in cancer cells may render the cancer cells vulnerable to be attacked by the human body's T-cells.

Figure 5:
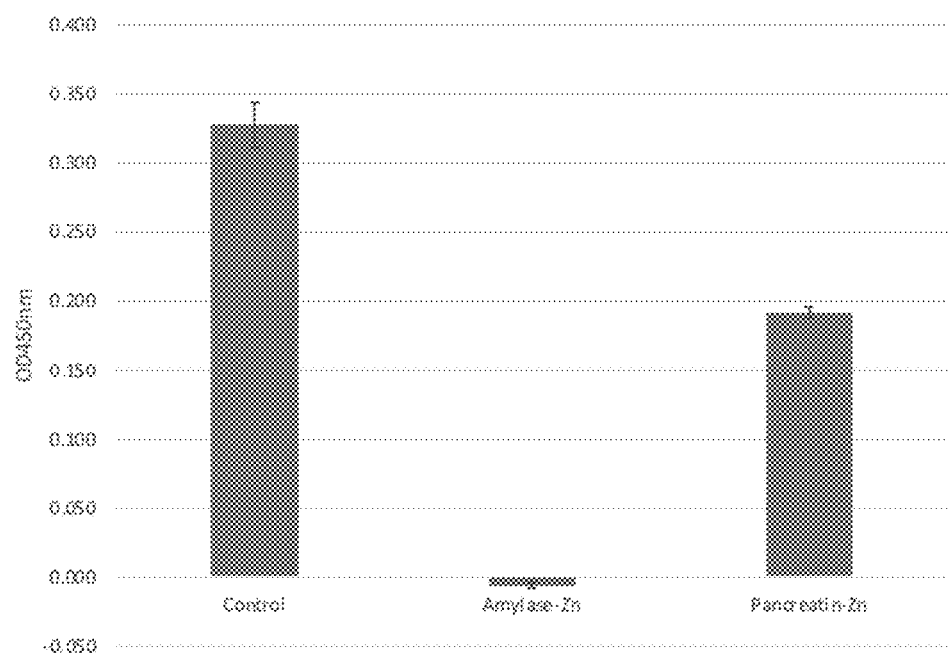
FIG. 5 is a bar graph comparing the PD-L1 expression in HT-29 cells that have been treated with either a control, with zinc-charged amylase, or with zinc-charged pancreatin.

As shown in FIG. 5, it is observed that the zinc-charged amylase, as well as zinc-charged pancreatin have strong suppression of PD-L1 expression on HT-29 cancer cells. FIG. 5 depicts a bar graph comparing the PD-L1 expression in HT-29 cells that have been treated with either a control of uncharged amylase, with zinc-charged amylase, or with zinc-charged pancreatin. It was observed that the HT-29 cells treated with the control exhibited a significant amount of PD-L1 expression. However, the HT-29 cells treated with zinc-charged pancreatin saw approximately a 42% reduction in PD-L1 expression, while the HT-29 cells treated with zinc-charged amylase saw the PD-L1 expression reduced to zero. This observation shows that administering zinc-charged amylase, as well as other zinc-charged pancreatic enzymes like zinc-charged pancreatin, may render the cancer cells vulnerable to be attacked by the T-cells of a human, such that the human's immune system may be able to attack and kill the cancer cells. This determination further supports the anticancer activity of zinc-charged amylase and other zinc-charged pancreatic enzymes.

Next, and as discussed below with respect to the mice testing and FIGS. 6A-6C, it was also observed that the zinc-charged amylase significantly reduced the secretion of TNF-a, IL-8, and IL-6 in mice, suggesting anti-inflammatory properties of the zinc-charged amylase. Specifically, it was observed that after mice were injected with LPS to induce inflammation, the levels of TNF-a, IL-8, and IL-6 in the mice were significantly reduced when the mice were fed zinc-charged amylase.

Normally, and as seen in the control, TNF-a, IL-8, and IL-6 are produced as an immune response to inflammation in the body. However, when the mice were given zinc-charged amylase then injected with LPS, the amounts of TNF-a, IL-8, and IL-6 were significantly reduced. This observation suggests that the zinc-charged amylase also has anti-inflammatory activity along with the anticancer activity observed.

Next, it was similarly observed that the zinc-charged amylase further played a role in the down regulation of the expression of oncogene C-Myc in HT-29 cell lines. A mutation in the C-Myc oncogene may cause a normal cell to become cancerous. Thus, if the amount of C-Myc in a cancer cell line is reduced, it may suggest anticancer activity. Here, when the HT-29 cells having the C-Myc oncogene were incubated with the zinc-charged amylase, it was observed that the amount of C-Myc in the HT-29 cancer cell line was significantly reduced. Thus, this observation further supports zinc-charged amylase having anticancer activity.

Lastly, it was observed that the zinc-charged amylase suppressed of the growth of breast cancer in mice. While this testing will be discussed in detail with the examples below, it was observed that the tumor volume of a breast cancer tumor in a MDA-MB-23 mice model was significantly suppressed when the zinc-charged amylase was injected into the mice. This observation further supports zinc-charged amylase having anticancer activity.

Each of these observations taken together indicate that once amylase is charged with zinc ions, the zinc-charged amylase have anticancer and anti-inflammatory properties that are activated. As such, zinc-charged amylase may be used as a cancer treatment or a treatment for inflammation.

B. Zinc-Charged Trypsin

Another pancreatic enzyme determined to induce apoptosis in cancer cells and trophoblasts is trypsin. Uncharged trypsin does not have any anticancer activity and does not induce apoptosis in cancer cells or trophoblasts. However, once the trypsin was charged with zinc ions, the zinc-charged trypsin began demonstrating apoptotic activity in cancer cell lines, suggesting the anticancer activity of this zinc-charged pancreatic enzyme.

Figure 15:
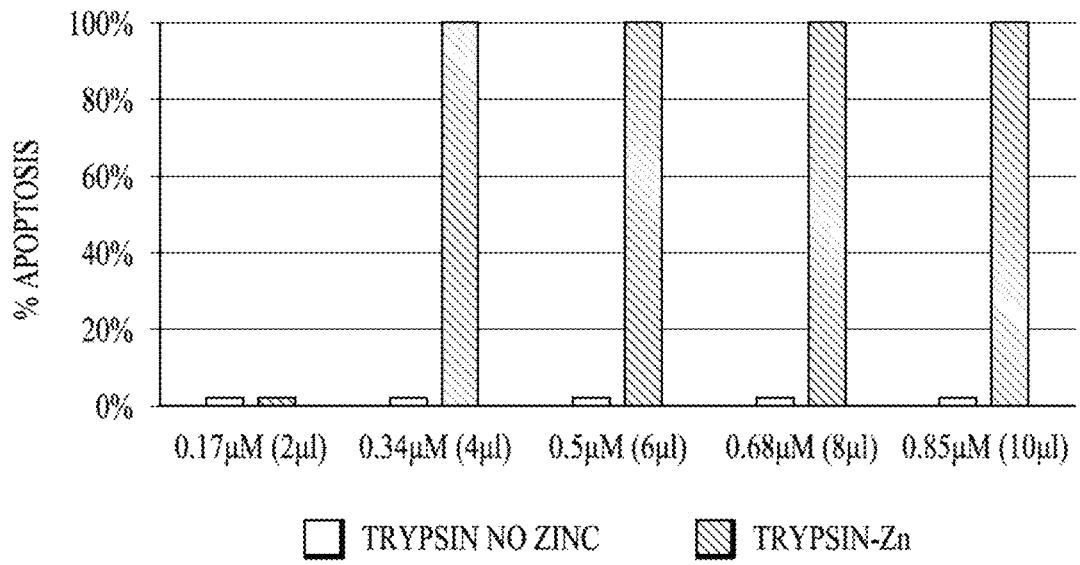
FIG. 15 is a bar graph showing the percent of apoptosis in HT-29 cancer cells when treated with uncharged trypsin versus zinc-charged trypsin.
Figure 16:
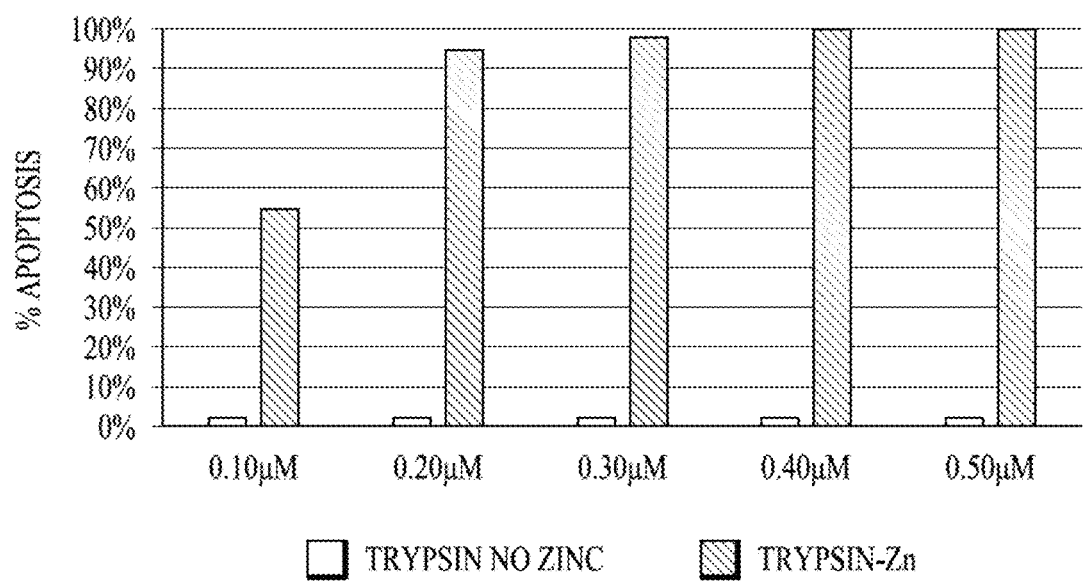
FIG. 16 is a bar graph showing the percent of apoptosis in placenta cells when treated with uncharged trypsin versus zinc-charged trypsin.

As shown in FIGS. 15-16, the zinc-charged trypsin exhibited apoptotic activity in both HT-29 cancer cells as well as placenta cells, while the uncharged trypsin exhibited no apoptotic activity whatsoever. FIG. 15 depicts a bar graph showing the percent of apoptosis in HT-29 cancer cells when treated with uncharged trypsin versus zinc-charged trypsin. The uncharged trypsin and zinc-charged trypsin were incubated with the HT-29 cells for 12 hours at five separate concentrations to determine the percent of apoptosis in the HT-29 cancer cells. As shown in FIG. 15, not one concentration of the uncharged trypsin produced any significant apoptosis in the HT-29 cancer cells. However, at the concentration of 0.34 µM and greater, 100% apoptosis in the HT-29 cancer cells induced by the zinc-charged trypsin was observed. This observation further suggests that the zinc-charged trypsin contains anticancer activity.

FIG. 16 shows a bar graph showing the percent of apoptosis in placenta cells when treated with uncharged trypsin versus zinc-charged trypsin. The uncharged trypsin and zinc-charged trypsin were incubated with the placenta cells at five separate concentrations to determine the percent of apoptosis in the placenta cells. As shown in FIG. 16, not one concentration of the uncharged trypsin produced any significant apoptotic activity in the placenta cells. However, at the concentration of 0.10 µM and greater, apoptosis induced by the zinc-charged trypsin in the placenta cells was observed. The greater the concentration of zinc-charged trypsin, the greater the apoptosis effect on the placenta cells, with 100% apoptosis measured when 0.40 µM of zinc-charged trypsin was administered. This observation further suggests that the zinc-charged trypsin induces apoptosis in trophoblasts, further suggesting the anticancer activity of the zinc-charged trypsin.

As discussed below with respect to the human saliva testing, the human subject testing performed on the zinc-charged trypsin further confirmed that zinc-charged trypsin contains anticancer activity. The HT-29 cancer cell line and BXPC3 cancer cell line (pancreatic cancer) had apoptosis induced by a single dose of zinc-charged trypsin. Further, this apoptotic activity was observed in the saliva of the subject who was given a single dose of the zinc-charged trypsin, suggesting that the anticancer activity of zinc-charged trypsin is orally available as well.

C. Other Zinc-Charged Pancreatic Enzymes

Similar to zinc-charged amylase and zinc-charged trypsin, other pancreatic enzymes were able to induce apoptosis in the HT-29 cancer cell line once these other pancreatic enzymes were charged with zinc. To determine the ability of these other pancreatic enzymes to induce apoptosis in the HT-29 cancer cell line, the IC50 activity of each zinc-charged pancreatic enzyme was measured. IC50 is a quantitative measure that indicates how much of a particular inhibitory substance is needed to inhibit a given biological process or biological component by 50%.

The IC50 activity of specific zinc-charged pancreatic enzymes on inducing apoptosis in the HT-29 cell line is as follows: Alpha-amylase (IC50=0.12 µM); Trypsin (IC50=0.1 µM); Elastase (IC50=1.1 µM); Carboxypeptidase (IC50=1.8 µM); and Chymotrypsin (IC50=1.0 µM). Additionally, the pancreatic hormone insulin, once zinc-charged by the disclosed method, has also been shown to induce apoptosis in the HT-29 cell line, having an IC50 activity of 40 nM.

These findings suggest that the induction of apoptosis in cancer cells by zinc-charged pancreatic enzymes is a ubiquitous phenomenon, further supporting the idea that zinc-charged pancreatic enzymes may be used as an anticancer agent.

2. Method of Preparing Zinc-Charged Pancreatic Enzymes

A method of preparing zinc-charged pancreatic enzymes is also disclosed. The general method of preparing the zinc-charged pancreatic enzymes includes (1) incubating a pancreatic enzyme with a chelating agent, (2) incubating the mixture from step 1 with a zinc compound, which results in a pancreatic enzyme charged with zinc ions, (3) separating the zinc-charged pancreatic enzyme from the solution from step (2), and (4) drying the zinc-charged pancreatic enzyme compound. The separation in step (3) may be accomplished by dialyzed the solution with deionized water to help separate the zinc-charged pancreatic enzymes from the solution from step (2). Additionally, the drying in from step (4) may be accomplished by lyophilization. While dialysis and lyophilization are preferred methods for separating and drying the zinc-charged pancreatic enzymes, other methods of separating and drying the zinc-charged pancreatic enzymes may be used without departing from the concepts disclosed herein.

In a preferred embodiment, the chelating agent may be ethylenediaminetetraacetic acid ("EDTA"). In other embodiments, other chelating agents, including but not limited to dimercaprol, dimercaptosuccinic acid ("DMSA"), and egtazic acid ("EGTA"), may be utilized as the chelating agent without departing from the concepts disclosed herein.

In a preferred embodiment, the zinc compound is zinc acetate. In other embodiments, other zinc compounds, including but not limited to zinc oxide, zinc sulfate, and zinc nitrate, may be used as the zinc compound. Any zinc compound may be used so long as the compound is capable of producing zinc ions to charge the pancreatic enzymes.

A preferred embodiment of the above method includes the following steps: (1) incubating a pancreatic enzyme with a chelating agent for at least one hour; (2) incubating the resulting solution from step 1 with a zinc compound for two to three hours; (3) dialyzing the resulting solution from step 2 against deionized water for three hours; and (4) drying the resulting solution from step 3 by lyophilization. In this preferred embodiment, the method may begin with 0.6 mM of the pancreatic enzyme, the chelating agent may be 5 mM ETDA, and the zinc compound may be 50 mM zinc acetate. Once these steps are followed, the result will be a zinc-charged pancreatic enzyme that may be used to treat cancer and/or inflammation.

The above method is described in general terms with to the pancreatic enzymes because any pancreatic enzyme may be zinc-charged using the above method. Further, as discussed above, each of the pancreatic enzymes, once zinc-charged through the above method, exhibit apoptotic activity against cancer cells.

3. Method of Treating Cancer & Inflammation Using Zinc-Charged Pancreatic Enzymes As these zinc-charged pancreatic enzymes have been shown to contain anticancer and anti-inflammatory activity, a method for treating cancer and inflammation using the zinc-charged pancreatic enzymes is also disclosed. The method of treating cancer using the zinc-charged pancreatic enzymes includes inducing apoptosis in cancer cells by administering the zinc-charged pancreatic enzyme to a cancer cell. The method of treating inflammation using the zinc-charged pancreatic enzymes includes reducing inflammation by administering the zinc-charged pancreatic enzyme to an inflamed cell. In this method, any of the zinc-charged pancreatic enzymes may be used to treat either cancer or inflammation through the above method.

4. Mouse Testing for Anticancer and Anti-Inflammatory Activity

The anti-cancer and anti-inflammatory activity of the zinc-charged pancreatic enzymes was observed in testing on mice. The following description of these tests performed on mice further suggest the anticancer and anti-inflammatory activity of the zinc-charged pancreatic enzymes. For the testing on mice, zinc-charged amylase was primarily used. However, based upon the above observations with respect to other zinc-charged pancreatic enzymes, it is expected that the results for the zinc-charged amylase will be representative of the other pancreatic enzymes once zinc-charged.

Figure 4:
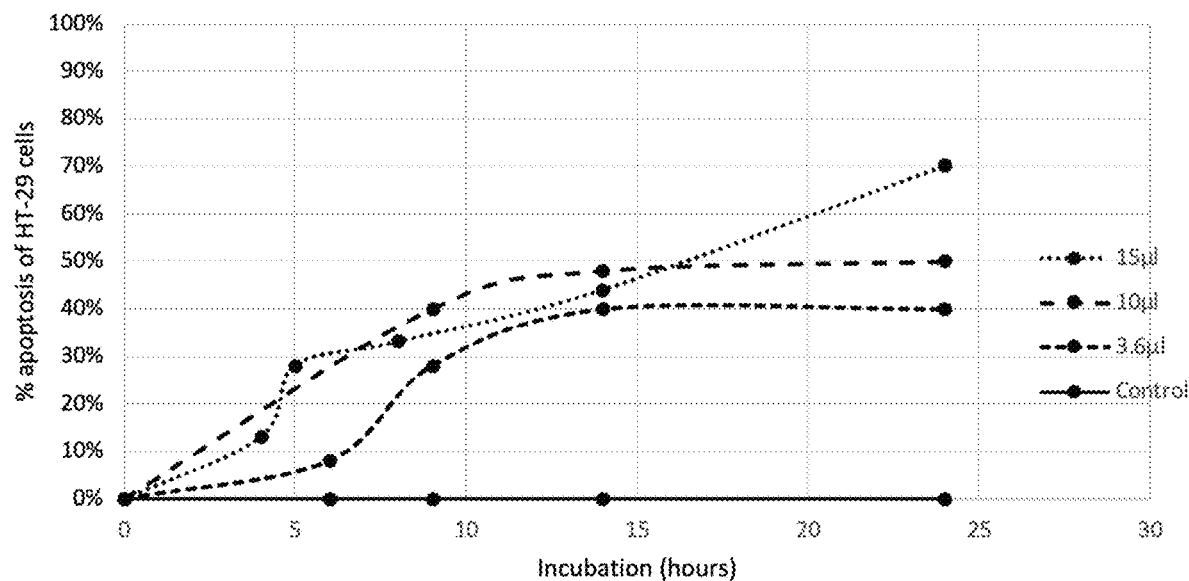
FIG. 4 is a line graph showing the percent of apoptotic activity of pancreas extract taken from mice that were fed with zinc-charged amylase on HT-29 cancer cells compared to a control.

FIG. 4 depicts a graph showing the apoptotic activity of pancreas extract taken from mice that were fed zinc-charged amylase. In this test, mice were orally fed 0.2 mg of zinc-charged amylase for seven days. After seven days, pancreas homogenate was collected from each mouse. The pancreas homogenate was then placed on HT-29 cancer cells in various concentrations, and the percentage of apoptosis was recorded over a 24-hour period of incubation time. The concentrations of the pancreas homogenate were 3.6 µL, 10 µL, and 15 µL. The control for this test followed the same protocol except the mice was fed uncharged amylase for seven days instead of zinc-charged amylase.

As shown in FIG. 4, the control pancreas homogenate did not exhibit any apoptotic activity in the HT-29 cancer cells. This was expected as uncharged amylase does not have any anticancer activity. However, the apoptotic activity in the zinc-charged amylase was observed in increasing levels with increasing concentrations. The lower dose of 3.6 µL of pancreas homogenate displayed up to 40% apoptotic activity, reaching this level at the 14-hour mark. The middle dose of 10 µL of pancreas homogenate displayed up to 50% apoptotic activity, also reaching this level at the 14-hour mark. The higher dose of 20 µL of pancreas homogenate displayed up to 70% apoptotic activity. This higher dose also does not appear to have peaked at the 24-hour mark, as the percentage of apoptosis had not leveled out by the 24-hour mark as with the 3.6 µL and 10 µL doses. Thus, had the 20 µL dose been allowed to be incubated with the HT-29 cells beyond the 24-hour mark, it is expected that further apoptotic activity greater than 70% would be observed.

The findings and observations from FIG. 4 confirm multiple theories related to the anticancer activity of zinc-charged pancreatic enzymes like zinc-charged amylase. First, these observations shows that the zinc-charged amylase has biodistribution to the pancreas, as the pancreas homogenate extracted from the mice produced the apoptotic activity in the HT-29 cancer cell line. This apoptotic activity would not be expected had the zinc-charged amylase not been biodistributed to the pancreas of the mice. Next, these observations confirm that pancreas homogenate extracted from mice who were fed the zinc-charged amylase for 7-days had anti-cancer properties, as they were capable of inducing apoptosis in the HT-29 cells. Lastly, these observations show that the anticancer properties of the zinc-charged amylase is dose dependent, as the higher concentrations of pancreas homogenate resulted in higher percentages of apoptosis in the HT-29 cells. These findings together further confirm the anticancer activity of pancreatic enzymes once charged with zinc.

Figure 8:
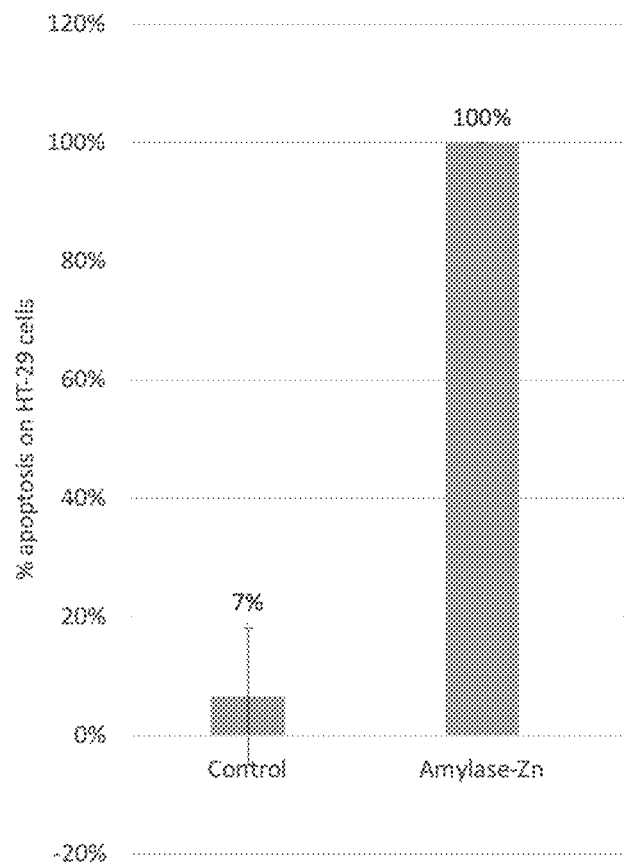
FIG. 8 is a bar graph showing the in vivo activity of zinc-charged amylase in the pancreas compared to a control.

FIG. 8 further corroborates the findings from FIG. 4 discussed above. FIG. 8 depicts a bar graph showing the in vivo activity of zinc-charged amylase in the pancreas. For this test, mice were orally given zinc-charged amylase, or a control for three days. For this test, the control was uncharged amylase. Once the mice were fed these two separate compositions, pancreas extract was extracted from the mice, and the apoptotic activity of HT-29 cells were evaluated.

As shown in FIG. 8, the zinc-charged amylase induced 100% apoptosis on the HT-29 cells, while the control only produced 7% apoptotic activity on the HT-29 cells. This test further confirms the findings of FIG. 4, namely, that the zinc-charged amylase is biodistributed to the pancreas and the pancreas extract with the zinc-charged amylase exhibits anticancer activity.

Figure 9:
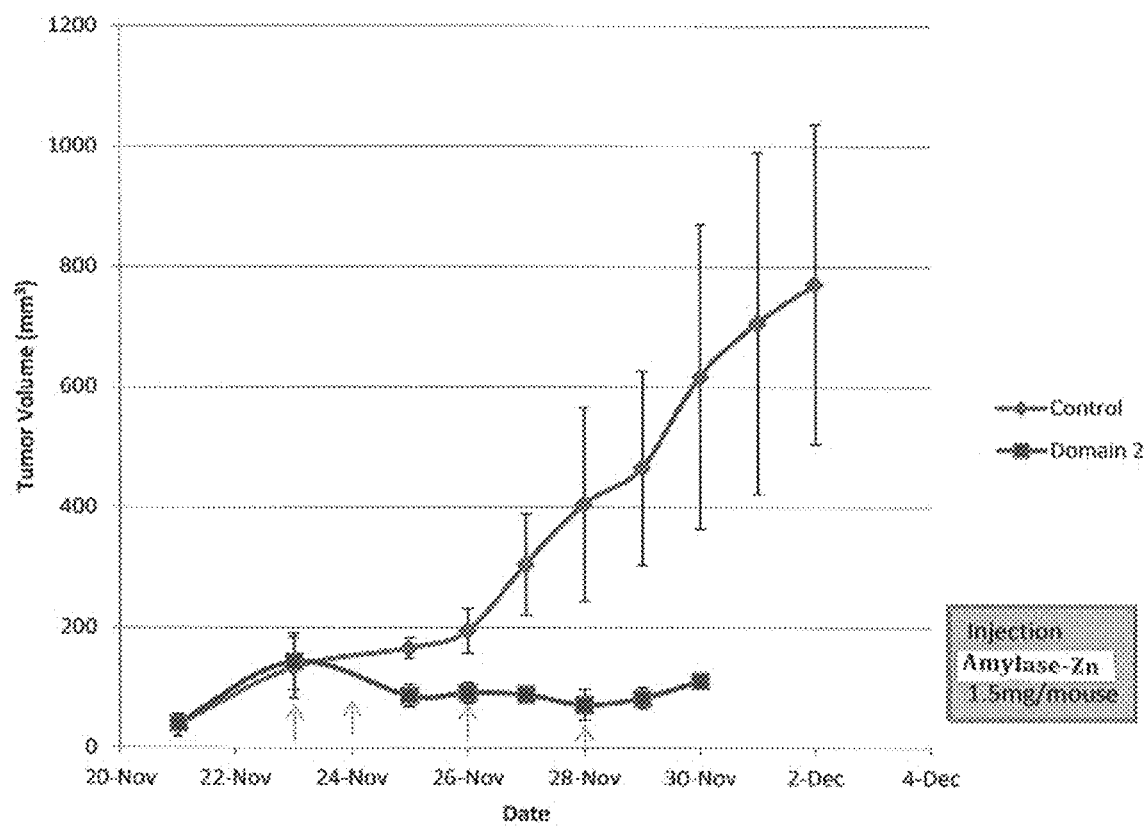
FIG. 9 is a line graph showing the suppression of the growth of a breast cancer tumor in an MDA-MB-23 mice model due to the administration zinc-charged amylase compared to a control.

The last test supporting the anticancer activity of zinc-charged amylase is shown in FIG. 9. FIG. 9 depicts a line graph showing the suppression of the growth of breast cancer in an MDA-MB-23 mice model. Specifically, FIG. 9 shows the comparison of tumor volume in a control versus a "domain 2" experimental group over a span of twelve days. The control mice were injected with 1.5 mg of uncharged amylase per mouse, while the "domain 2" experimental group mice were injected with 1.5 mg of zinc-charged amylase per mouse.

As shown in FIG. 9, the mice who were given the control did not see any suppression of breast cancer growth. The control mice saw the breast cancer tumor volume increase to over 600 mm$^3$ by day ten of the study and reached a maximum of nearly 800 mm$^3$ by day twelve. However, the mice who were injected with the zinc-charged amylase saw significant suppression of the breast cancer growth, with the breast cancer tumor volume never exceeding 200 mm$^3$ over the same ten-day period. Thus, it is observed that the zinc-charged amylase was able to suppress breast cancer growth in mice, further confirming the anticancer activity of zinc-charged pancreatic enzymes such as zinc-charged amylase.

Further, the testing on mice also showed the anti-inflammatory activity of the zinc-charged pancreatic enzymes. FIGS. 6A-6C (together FIG. 6) show the effects of zinc-charged amylase on the IL-6, IL-8, and TNF-a levels in mouse serum. For this test, mice were fed 0.26 mg of zinc-charged amylase for seven days. On the eighth day, the mice were injected with 1 mg LPS to induce inflammation. Control mice who were fed with uncharged amylase were also injected with 1 mg LPS to induce inflammation. Two hours after injection, sera were collected from the control mice and the mice fed the zinc-charged amylase, and the IL-6, IL-8, and TNF-a levels were compared using a standard ELISA kit.

Figure 6A:
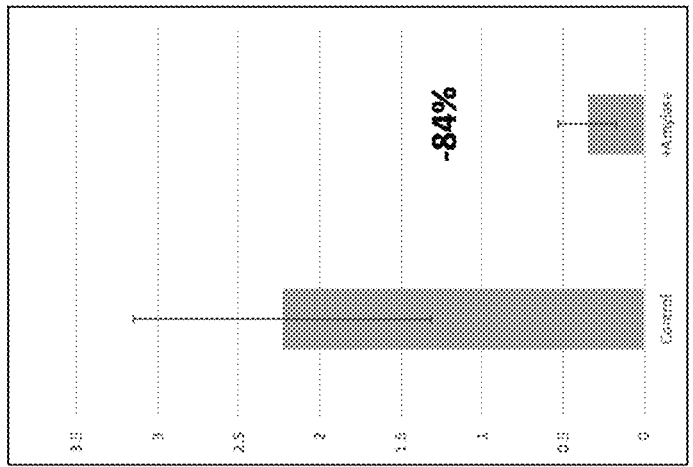
FIG. 6A is a bar graph showing the effects of zinc-charged amylase on the TNF-α levels in mouse serum compared to a control.
Figure 6B:
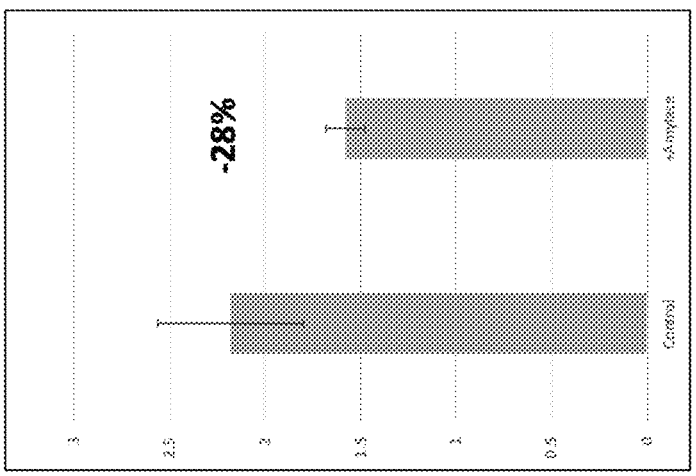
FIG. 6B is a bar graph showing the effects of zinc-charged amylase on the IL-8 levels in mouse serum compared to a control.
Figure 6C:
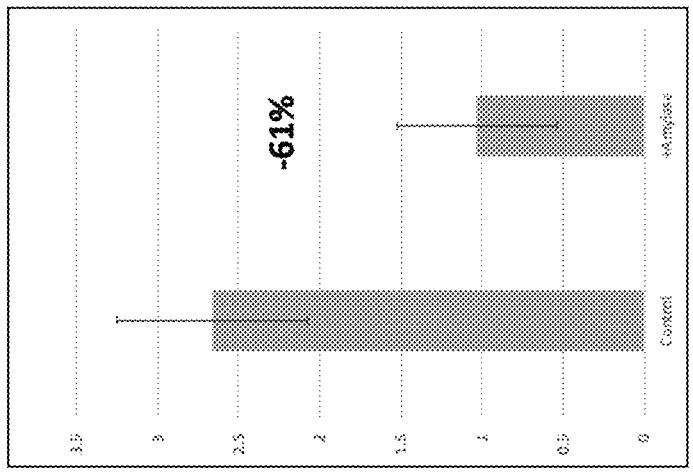
FIG. 6C is a bar graph showing the effects of zinc-charged amylase on the IL-6 levels in mouse serum compared to a control.

As shown in FIG. 6A, the level of TNF-a in the serum of the mice who were fed the zinc-charged amylase showed an 84% reduction in TNF-a levels when compared to the control. As shown in FIG. 6B, the level of IL-8 in the serum of the mice who were fed the zinc-charged amylase showed an 28% reduction in IL-8 levels when compared to the control. As shown in FIG. 6C, the level of IL-6 in the serum of the mice who were fed the zinc-charged amylase showed an 61% reduction in IL-6 levels when compared to the control. Thus, the significant reduction in the levels of these compounds when compared to the control indicates that the zinc-charged amylase has anti-inflammatory activity as well as the anticancer activity.

Figures 10A, 10B, 10C:
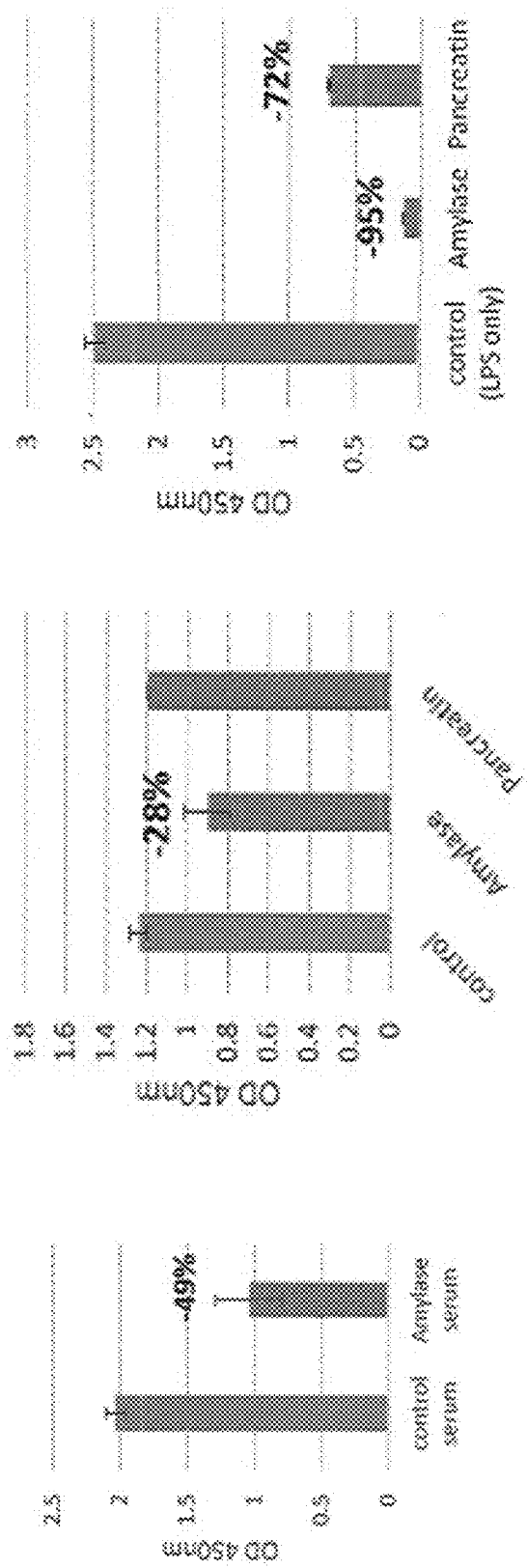
FIG. 10A is a bar graph showing the effects of zinc-charged amylase on the IL-6 levels in mouse serum compared to a control.
FIG. 10B is a bar graph showing the effects of zinc-charged amylase and zinc-charged pancreatin on the IL-8 levels in mouse serum compared to a control.
FIG. 10C is a bar graph showing the effects of zinc-charged amylase and zinc-charged pancreatin on the on the TNF-a levels in mouse serum compared to a control.
Figures 11A, 11B:
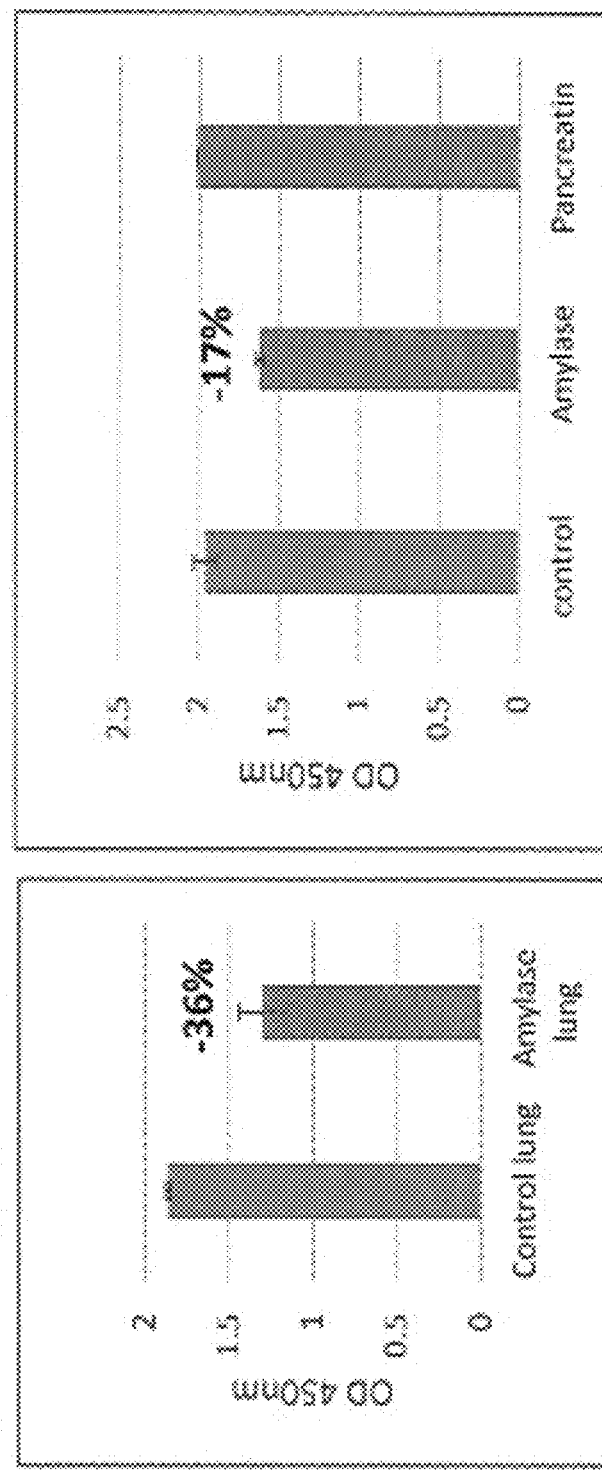
FIG. 11A is a bar graph showing the effects of zinc-charged amylase on the IL-6 levels in mouse lung tissue compared to a control.
FIG. 11B is a bar graph showing the effects of zinc-charged amylase and zinc-charged pancreatin on the IL-8 levels in mouse lung tissue compared to a control.

These observations regarding the anti-inflammatory activity of the zinc-charged pancreatic enzymes were further corroborated by FIGS. 10A-10C (together FIG. 10) and FIGS. 11A-11B (together FIG. 11). FIG. 10 and FIG. 11 each show the effects of zinc-charged pancreatic enzymes on the IL-6, IL-8, and TNF-a levels in serum and in lung tissue. The protocol for these tests were consistent. Each group of mice was either administered zinc-charged amylase, zinc-charged pancreatin, or no pancreatic enzyme as the control. For the mice receiving zinc-charged amylase, 0.5 mg of zinc-charged amylase per mouse was administered for three days. For the mice receiving zinc-charged pancreatin, 0.66 mg of zinc-charged pancreatin per mouse was administered for three days. The control mice were not given either pancreatic enzyme. Afterward, 1 mg/kg of LPS was administered to each group of mice, including the control. Two hours later, serum or lung tissue was collected from the mice to determine the levels of IL-6, IL-8, and TNF-a.

First, FIG. 10 depicts the levels of IL-6, IL-8, and TNF-a in mouse serum after administration of either a control, the zinc-charged amylase, or the zinc-charged pancreatin. As shown in FIG. 10A, the zinc-charged amylase lowered the IL-6 levels in the mouse serum by 49% when compared to the control. As shown in FIG. 10B, the zinc-charged amylase lowered the IL-8 levels in the mouse serum by 28% when compared to the control. However, the zinc-charged pancreatin did not have any effect on the levels of IL-8 in this test. As shown in FIG. 10C, the zinc-charged amylase and zinc-charged pancreatin lowered the TNF-a levels in the mouse serum by 95% and 72% respectively when compared to the control. Thus, this test suggests that the zinc-charged amylase is capable of lowering the IL-6, IL-8, and TNF-a levels in a subject, thus confirming the anti-inflammatory activity of the zinc-charged amylase. The zinc-charged pancreatin was not effective in lowering the IL-6 or IL-8 levels in the mouse serum but was effective in lowering the TNF-a levels. This further suggests that the other zinc-charged pancreatic enzymes are also capable of anti-inflammatory activity.

FIG. 11 depicts the resulting levels of IL-6 and IL-8 in mouse lung tissue after administration of either a control, the zinc-charged amylase, or zinc-charged pancreatin. As shown in FIG. 11A, the zinc-charged amylase lowered the IL-6 levels in the mouse lung tissue by 36% when compared to the control. As shown in FIG. 11B, the zinc-charged amylase lowered the IL-8 levels in the mouse lung tissue by 17% when compared to the control. However, the zinc-charged pancreatin did not have any effect on the levels of IL-8 in the lung tissue in this test. Thus, this test suggests that the zinc-charged amylase is capable of lowering the IL-6 and IL-8 levels in lung tissues, while simultaneously confirming the results from the testing on the mouse serum.

Overall, FIGS. 10 and 11 both indicate that zinc-charged pancreatic enzymes are capable of reducing the molecules responsible for the inflammation immune response, thereby providing anti-inflammatory activity. Thus, this testing on mouse serum and lung tissue confirms the anti-inflammatory activity of the zinc-charged pancreatic enzymes.

5. Human Saliva Testing for Anticancer Activity

Testing done on human saliva after the oral ingestion of the zinc-charged pancreatic enzymes also demonstrates both the anticancer activity and oral availability of these pancreatic enzymes once charged with zinc. For each of these tests on human subjects, a zinc-charged pancreatic enzyme was ingested by a human subject, and saliva was collected at different periods of time post-ingestion. The saliva samples were then placed on HT-29 cancer cells, and the apoptotic activity was assessed after incubation of the HT-29 cancer cells with the saliva. Ultimately, these tests showed that the zinc-charged pancreatic enzymes have oral bioavailability that can be detected in the saliva, further confirming the anticancer activity of these zinc-charged pancreatic enzymes.

Figure 7:
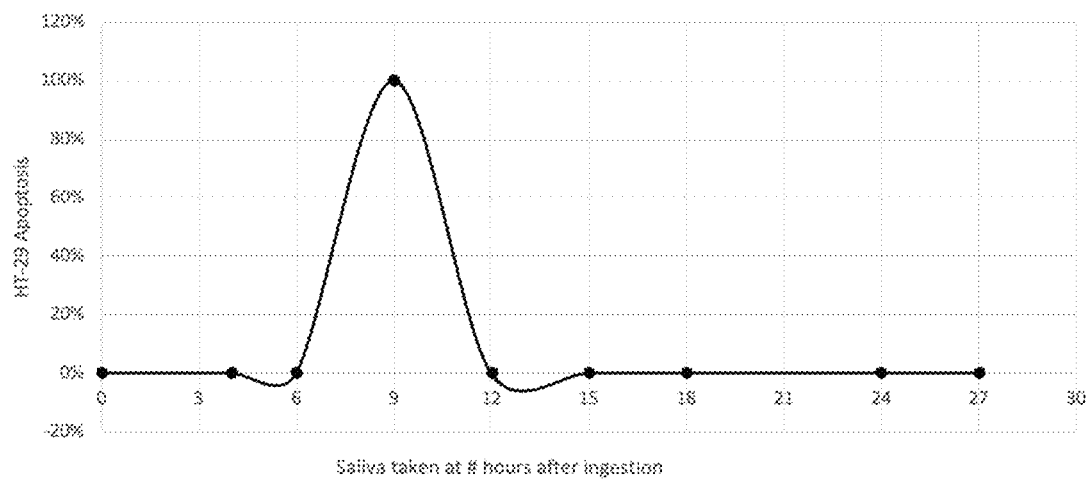
FIG. 7 is a line graph showing the percent of apoptotic activity in HT-29 cells after being incubated with saliva collected at different times after a human subject ingested zinc-charged amylase.

FIG. 7 depicts a line graph showing the percent of apoptotic activity in HT-29 cells after being incubated with saliva collected at different times post-ingestion of zinc-charged amylase. For this test, 200 mg of zinc-charged amylase was ingested by a human subject. Saliva from the human subject was collected at 4-, 6-, 9-, 12-, 15-, 18-, 24-, and 27-hour post-ingestion. The saliva samples were then placed on HT-29 cancer cells, and the apoptotic activity was assessed after incubating the saliva samples with the HT-29 cancer cells for 20 hours. As shown in FIG. 7, the saliva sample collected at the 9th hour post-ingestion induced 100% apoptosis in the HT-29 cancer cells. Thus, FIG. 7 shows that the zinc-charged amylase has oral bioavailability that is detectable in saliva, with the peak activity in the saliva detected 9 hours post-ingestion. This human study further confirms the anticancer activity of the zinc-charged pancreatic enzymes, and specifically zinc-charged amylase.

Figure 17:
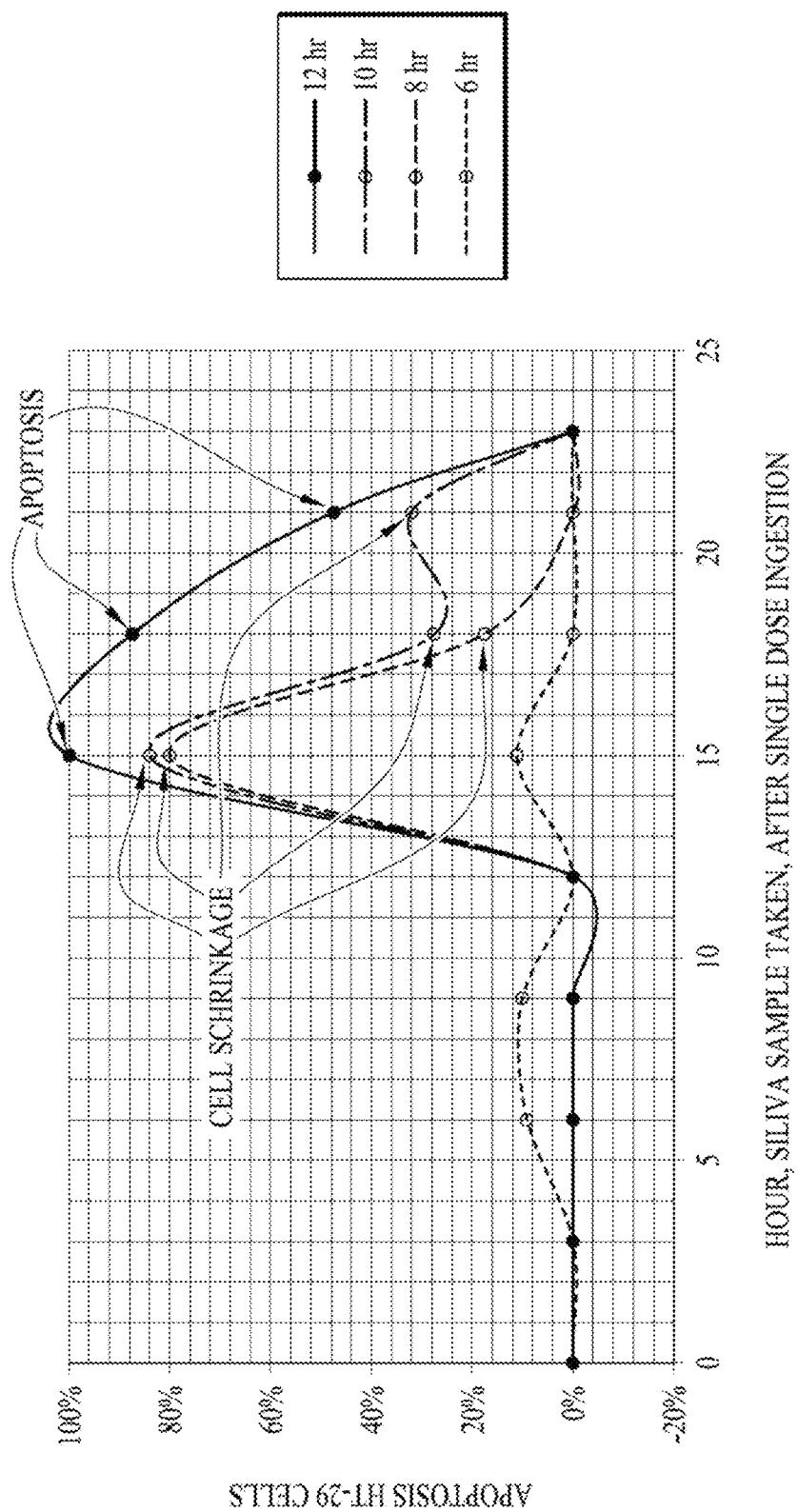
FIG. 17 is a line graph showing the percent of apoptosis in HT-29 cancer cells and that were incubated with saliva from a human subject who was orally administered whole protein zinc-charged amylase.

This observation is further confirmed by the testing shown in FIG. 17, which depicts the percent of apoptosis in HT-29 cancer cells that were incubated with saliva from a human subject who was orally administered whole protein zinc-charged amylase. For this specific test, 25 mg of whole protein zinc-charged amylase (IC50=25 nM) was administered to a human subject in a single dose, and saliva samples were taken at 3-, 6-, 9-, 12-, 15-, 18-, 21-, and 23-hours post-ingestion. Each of these saliva samples were then tested for HT-29 apoptotic activity by incubating each saliva sample with HT-29 cells for 6-hours, 8-hours, 10-hours, or 12-hours.

As shown in FIG. 17, the saliva samples exhibited some apoptotic activity for all four incubation times. The saliva samples incubated for 6 hours only displayed minor apoptotic activity, having peak apoptotic activity at the 6-hour, 9-hour, and 15-hour post-ingestion saliva samples. While these tests displayed minimal apoptotic activity, the fact that any apoptotic activity exists in the saliva of a human subject indicates that the zinc-charged amylase contains some anticancer activity. However, the saliva samples incubated with HT-29 cancer cells for 8-, 10-, and 12-hours all showed significant apoptotic activity, with the 12-hour incubation showing 100% apoptosis of the HT-29 cancer cells. Further, while the 8- and 10-hour incubation times did not reach 100% apoptosis of the HT-29 cancer cells like the 12-hour incubation, these two incubation times showed significant cell shrinkage resulting from the significant percent of apoptosis in the HT-29 cells. This was especially prevalent for the saliva collected 15-hours post-ingestion. Thus, this data confirms the anticancer activity of the zinc-charged amylase, as well as the oral bioavailability of the zinc-charged amylase in saliva post-ingestion.

Figure 12:
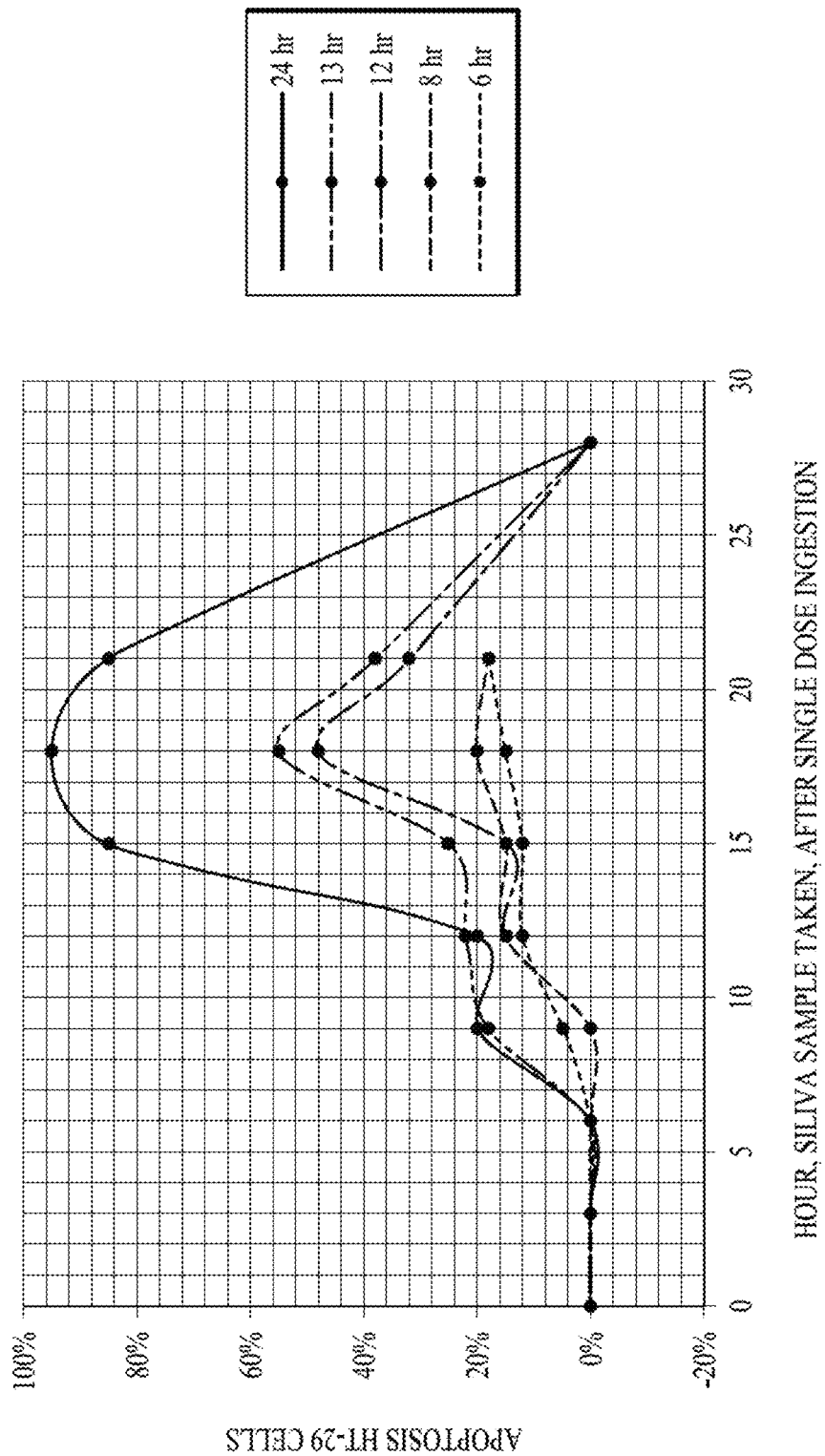
FIG. 12 is a line graph showing the percent of apoptosis in HT-29 cancer cells and that were incubated with saliva from a human subject who was orally administered whole protein zinc-charged trypsin.
Figure 13:
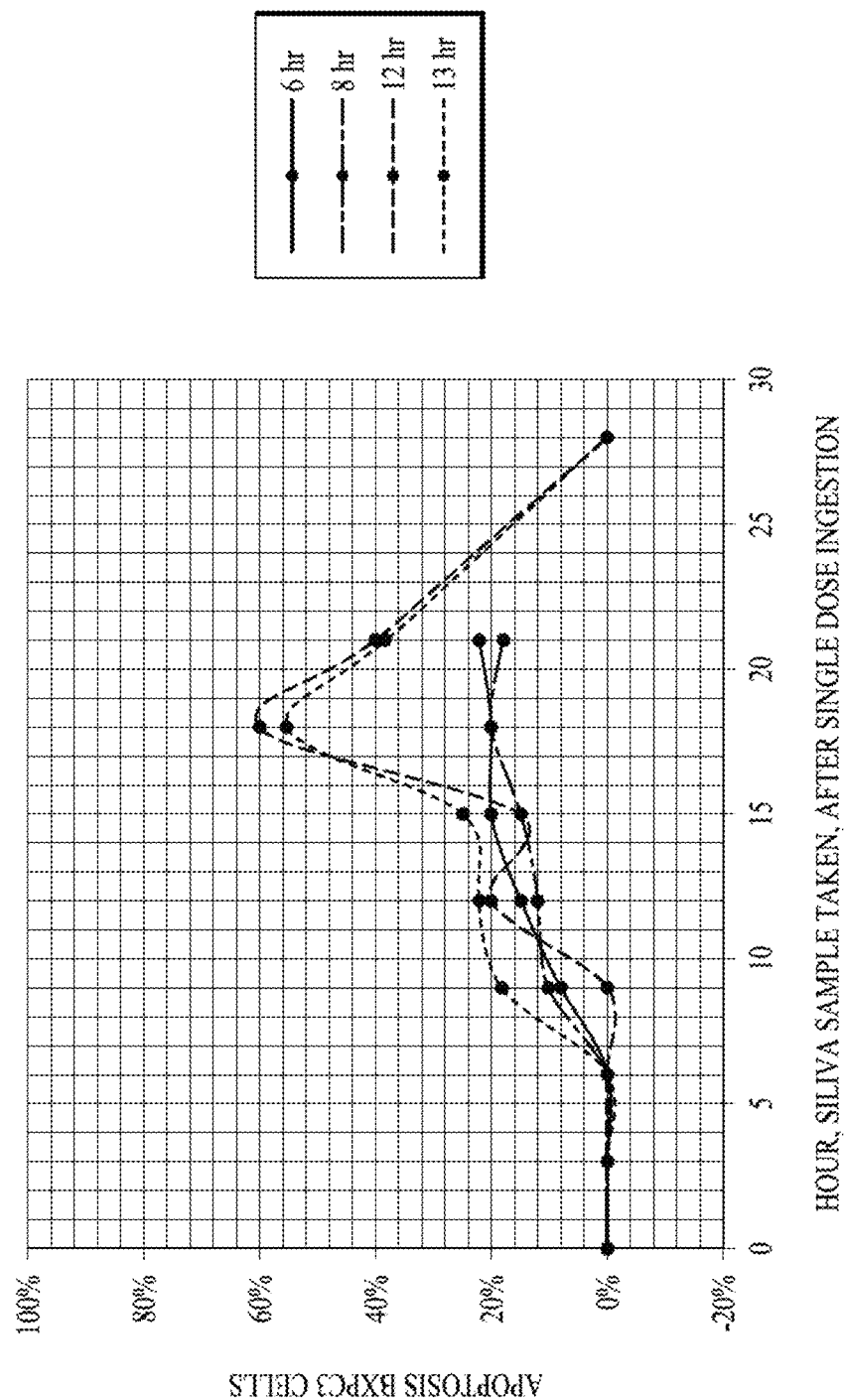
FIG. 13 is a line graph showing the percent of apoptosis in BXPC3 cancer cells and that were incubated with saliva from a human subject who was orally administered whole protein zinc-charged trypsin.
Figure 14:
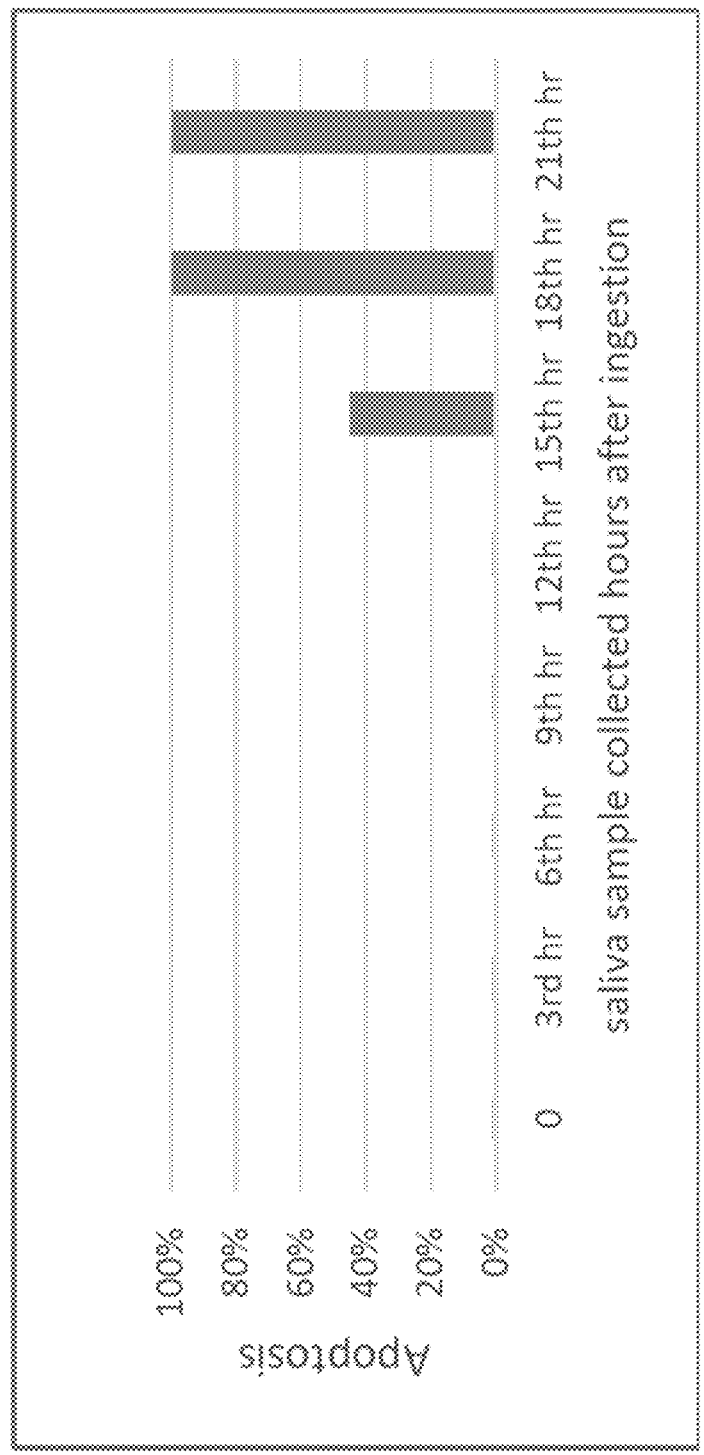
FIG. 14 is a bar graph showing the percent of apoptosis in HT-29 cancer cells and that were incubated with saliva from a human subject who was orally administered whole protein zinc-charged trypsin.

Further human testing was done with respect to other zinc-charged pancreatic enzymes, namely, zinc-charged trypsin, to determine whether this anticancer activity was ubiquitous across all pancreatic enzymes once charged with zinc. FIGS. 12-14 depict the test results for the apoptotic activity of whole protein zinc-charged trypsin in human saliva post ingestion. For these tests, a whole protein zinc-charged trypsin was ingested by a human subject, and saliva was collected at different periods of time post-ingestion. The saliva samples were concentrated by a factor of 10 then placed on HT-29 cancer cells and BXPC3 cancer cells, and the apoptotic activity was assessed after incubation of the cancer cells with the saliva. Further, some of the saliva collected was also concentrated then incubated with HT-29 cancer cells to determine the levels of apoptotic activity at different time periods post ingestion. Ultimately, these tests showed that not only zinc-charged amylase, but other zinc-charged pancreatic enzymes such as zinc-charged trypsin have oral bioavailability that can be detected in the saliva, further confirming the general anticancer activity of zinc-charged pancreatic enzymes.

As with FIG. 17, FIGS. 12 and 13 depict the percent of apoptosis in HT-29 cancer cells and BXPC3 cancer cells that were incubated with saliva from a human subject who was orally administered whole protein zinc-charged trypsin. For this specific test, 50 mg of whole protein zinc-charged amylase (IC50=50 nM) was administered to a human subject in a single dose, and saliva samples were taken at 3-, 6-, 9-, 12-, 15-, 18-, and 21-hours post-ingestion. Each of these saliva samples were concentrated by a factor of 10 then tested for HT-29 apoptotic activity by incubating each saliva sample with HT-29 cells for 6-hours, 8-hours, 12-hours, 13-hours, or 24-hours. Each of these saliva samples were also tested for BXPC3 apoptotic activity by incubating each saliva sample with BXPC3 cells for 6-hours, 8-hours, 12-hours, or 13-hours.

As shown in FIG. 12, the saliva samples exhibited some apoptotic activity for all five incubation times on HT-29 cancer cells. The saliva samples incubated for 6-hours displayed up to a 20% apoptotic activity, having peak apoptotic activity for the 21-hour post-ingestion saliva samples. The saliva sample incubated for 8-hours displayed nearly identical apoptotic activity to the 6-hour incubation sample. The samples incubated for 12- and 13-hours also displayed significant apoptotic activity, peaking at above 50% apoptotic activity for the 18-hour post-ingestion saliva sample. The sample incubated for 24-hours displayed nearly 100% apoptotic activity in the HT-29 cells, also peaking at 18-hours for the post-ingestion saliva sample. Thus, as with the prior testing data, the fact that apoptotic activity of HT-29 cells exists in the saliva of a human subject indicates that the zinc-charged trypsin, as well as all other zinc-charged pancreatic enzymes, contain anticancer activity. This is only further confirmed by the near 100% apoptotic activity for the saliva incubated with the HT-29 cells for 24 hours.

As shown in FIG. 13, the saliva samples also exhibited some apoptotic activity for all four incubation times on BXPC3 cancer cells. The saliva samples incubated for 6-hours displayed a little above 20% apoptotic activity, having peak apoptotic activity for the 21-hour post-ingestion saliva samples. The saliva sample incubated for 8-hours displayed nearly identical apoptotic activity to the 6-hour incubation sample, with the peak apoptosis occurring for the 18-hour post-ingestion saliva sample. The samples incubated for 12- and 13-hours also displayed significant apoptotic activity, peaking at 60% apoptosis for the 18-hour post-ingestion saliva sample. Here, the BXPC3 cells were unable to be incubated for longer than 13-hours, as the BXPC3 cells were no longer healthy for testing.

However, as the percent of apoptotic activity for the HT-29 cell line from FIG. 12 are very similar to the apoptotic activity for the BXPC3 cell line from FIG. 13 for the 6-, 8-, 12-, and 13-hour incubation times, it is expected that had the sample been incubated for 24-hours, it would have also displayed nearly 100% apoptotic activity in the BXPC3 cells, likely also peaking at 18-hours for the post-ingestion saliva sample. Additionally, both FIGS. 12 & 13 show that longer incubation times caused a higher rate of apoptosis.

Further confirming the strong apoptotic activity in saliva samples taken 18-hours post-ingestion or more is the graph shown in FIG. 14. FIG. 14 depicts saliva samples that were collected 3-, 6-, 9-, 12-, 15-, 18-, and 21-hours post-ingestion of zinc-charged trypsin, 10-times concentrated, and incubated with HT-29 cells for six hours to determine the apoptotic activity for each saliva sample. Originally, 100 µL of the saliva samples were collected, then concentrated down to 10 µL prior to incubation with the HT-29 cells.

The result depicted in FIG. 14 shows that there was no apoptotic activity in the saliva samples collected 3-, 6-, 9-, and 12-hours post-ingestion of zinc-charged trypsin. However, the apoptotic activity in the saliva began increasing at the 15-hour post-ingestion point, which had approximately 45% apoptotic activity. Ultimately, the saliva samples collected 18-hour post-ingestion and later exhibited 100% apoptotic activity on the HT-29 cells. This finding matches that of the findings in FIGS. 12 and 13, as well as FIG. 17, which each showed minimal apoptotic activity until the saliva sample taken 15-hours post ingestion of the zinc-charged pancreatic enzyme, with peak apoptotic activity being measured at 15- or 18-hours post ingestion point or later.

Therefore, these tests on human subjects further show that the zinc-charged pancreatic enzymes are capable of inducing apoptosis in various cancer cell lines. These tests have demonstrated that both zinc-charged amylase and zinc-charged trypsin have anticancer activity against the HT-29 cancer cell line and the BXPC3 cancer cell line. Further, these tests confirm that the zinc-charged pancreatic enzymes are orally bioavailable, in that the zinc-charged pancreatic enzymes can survive the acidic conditions of the stomach and be absorbed into the body and blood stream through the GI tract. Thus, these findings further confirm that pancreatic enzymes, once charged with zinc, have oral bioavailability and anticancer activity and may be used to treat cancer.

I claim:

1. A method of preparing a zinc-charged pancreatic enzyme, the method comprising:
   (1) incubating a pancreatic enzyme with a chelating agent;
   (2) incubating the resulting mixture from step (1) with a zinc compound, wherein said pancreatic enzyme is charged with zinc ions such that a zinc-charged pancreatic enzyme is formed; and
   (3) separating said zinc-charged pancreatic enzyme from the resulting mixture from step (2).

2. The method of claim 1, wherein said separation of said zinc-charged pancreatic enzymes is accomplished by dialysis.

3. The method of claim 1, further comprising:
   (4) drying said zinc-charged pancreatic enzyme.

4. The method of claim 3, wherein said drying of said zinc-charged pancreatic enzyme is accomplished by lyophilization.

5. The method of claim 1, wherein said pancreatic enzyme is amylase.

6. The method of claim 1, wherein said pancreatic enzyme is trypsin.

7. The method of claim 1, wherein said chelating agent is ethylenediaminetetraacetic acid.

8. The method of claim 1, wherein said zinc compound is zinc acetate.

9. A composition made by the method of claim 1, comprising:
   a zinc-charged pancreatic enzyme.

10. The composition of claim 9, wherein said zinc-charged pancreatic enzyme is zinc-charged amylase.

11. The composition of claim 9, wherein said zinc-charged pancreatic enzyme is zinc-charged trypsin.

12. The composition of claim 9, wherein said zinc-charged pancreatic enzyme is capable of treating cancer.

13. The composition of claim 12, wherein said zinc-charged pancreatic enzyme is zinc-charged amylase.

14. The composition of claim 12, wherein said zinc-charged pancreatic enzyme is zinc-charged trypsin.

15. The composition of claim 9, wherein said zinc-charged pancreatic enzyme is capable of treating inflammation.

16. The composition of claim 9, wherein said zinc-charged pancreatic enzyme is capable of being administered orally.

17. A method of inducing apoptosis in cancer cells of a subject comprising:
    administering a zinc-charged pancreatic enzyme to said subject, wherein said administration of said zinc-charged pancreatic enzyme induces apoptosis in said cancer cells.

18. The method of claim 17, wherein said zinc-charged pancreatic enzyme is zinc-charged amylase.

19. The method of claim 17, wherein said zinc-charged pancreatic enzyme is zinc-charged trypsin.

20. The method of claim 17, wherein said zinc-charged pancreatic enzyme is administered orally.

* * * * *